(12) United States Patent
Yaremchuk

(10) Patent No.: US 9,895,211 B2
(45) Date of Patent: Feb. 20, 2018

(54) CRANIOFACIAL IMPLANT REGISTRATION FEATURES AND METHODS

(76) Inventor: Michael J. Yaremchuk, Lynnfield, MA (US)

( * ) Notice: Subject to any disclaimer, the term of this patent is extended or adjusted under 35 U.S.C. 154(b) by 739 days.

(21) Appl. No.: 13/532,283

(22) Filed: Jun. 25, 2012

(65) Prior Publication Data

US 2012/0330427 A1    Dec. 27, 2012

Related U.S. Application Data

(63) Continuation of application No. 12/342,762, filed on Dec. 23, 2008.

(60) Provisional application No. 61/018,943, filed on Jan. 4, 2008, provisional application No. 61/018,952, filed on Jan. 4, 2008, provisional application No. 61/018,948, filed on Jan. 4, 2008.

(51) Int. Cl.
*A61F 2/02* (2006.01)
*A61F 2/00* (2006.01)

(52) U.S. Cl.
CPC .... *A61F 2/0059* (2013.01); *A61F 2250/0062* (2013.01)

(58) Field of Classification Search
CPC ........................................................ A61F 2/02
USPC ........................................................ 623/17.18
See application file for complete search history.

(56) References Cited

U.S. PATENT DOCUMENTS

| | | |
|---|---|---|
| 717,526 A | 1/1908 | Barney |
| 1,920,821 A | 8/1933 | Wassenaar |
| 2,665,692 A | 1/1954 | L'Esperance |
| 4,610,252 A | 9/1986 | Catalano |
| 4,764,168 A | 8/1988 | Suh |
| 4,803,983 A | 2/1989 | Siegel |
| 4,959,065 A | 9/1990 | Arnett et al. |
| 5,195,951 A | 3/1993 | Giampapa |
| 5,320,637 A | 6/1994 | Borders, Jr. |
| 5,380,329 A * | 1/1995 | Elia .................. A61B 17/58 606/330 |
| 5,391,181 A | 2/1995 | Johnson et al. |
| 5,421,831 A | 6/1995 | Giampapa |
| 5,496,371 A | 3/1996 | Eppley et al. |
| 5,514,179 A | 5/1996 | Brennan |
| 5,554,194 A * | 9/1996 | Sanders .................. 623/17.17 |
| 5,578,032 A | 11/1996 | Lalonde |
| 5,643,316 A | 7/1997 | Kaiser et al. |
| 5,658,516 A | 8/1997 | Eppley et al. |
| 5,971,775 A | 10/1999 | Tor et al. |
| RE37,249 E | 6/2001 | Leibinger et al. |
| 6,277,150 B1 | 8/2001 | Crawley et al. |
| 6,302,884 B1 | 10/2001 | Wellisz et al. |
| 6,551,608 B2 | 4/2003 | Yao |
| 6,582,435 B2 | 6/2003 | Wellisz et al. |
| D488,229 S | 4/2004 | Rinner et al. |

(Continued)

FOREIGN PATENT DOCUMENTS

RU    2074672 C1    3/1997

OTHER PUBLICATIONS

English Abstract, RU 2074672 C1, Beletskij Boris Ivanovich et al., Mar. 10, 1997.

(Continued)

*Primary Examiner* — Matthew Schall
(74) *Attorney, Agent, or Firm* — Goodwin Procter LLP

(57) ABSTRACT

Various embodiments of craniofacial implants, surgical instruments, and techniques are described to provide improved surgical results.

8 Claims, 23 Drawing Sheets

(56) References Cited

U.S. PATENT DOCUMENTS

| | | | |
|---|---|---|---|
| 7,008,455 | B2 | 3/2006 | Raphael et al. |
| 7,104,475 | B2 | 3/2006 | Mongold |
| 7,066,962 | B2 | 6/2006 | Swords |
| D540,264 | S | 4/2007 | Zhang |
| D606,496 | S | 12/2009 | Ngo |
| D608,293 | S | 1/2010 | Ngo |
| D610,548 | S | 2/2010 | Ngo |
| D621,364 | S | 8/2010 | Kasahara |
| D623,138 | S | 9/2010 | Ngo |
| 2003/0224654 | A1 | 12/2003 | Wu |
| 2004/0138591 | A1 | 7/2004 | Iseki et al. |
| 2005/0085850 | A1 | 4/2005 | Harris, Jr. et al. |
| 2006/0116682 | A1 | 6/2006 | Longo |
| 2006/0217813 | A1 | 9/2006 | Posnick et al. |
| 2006/0224242 | A1 | 10/2006 | Swords et al. |
| 2007/0067041 | A1 | 3/2007 | Kotoske |
| 2007/0156171 | A1 | 7/2007 | Lang et al. |
| 2010/0112834 | A1 | 5/2010 | Chen et al. |
| 2010/0184339 | A1 | 7/2010 | Ngo et al. |

OTHER PUBLICATIONS

Ramirez, "Mandibular Matrix Implant System: A Method to Restore Skeletal Support to the Lower Face," Jul. 2000, vol. 106(1), pp. 176-189.

Yaremchuk, "Atlas of Facial Implants", Elsevier, © 2007, 244 pages.

Zienowicz et al., "A Microsurgical Suction Mat", The Journal of Hand Surgery, 1994, 19A, 519-520.

\* cited by examiner

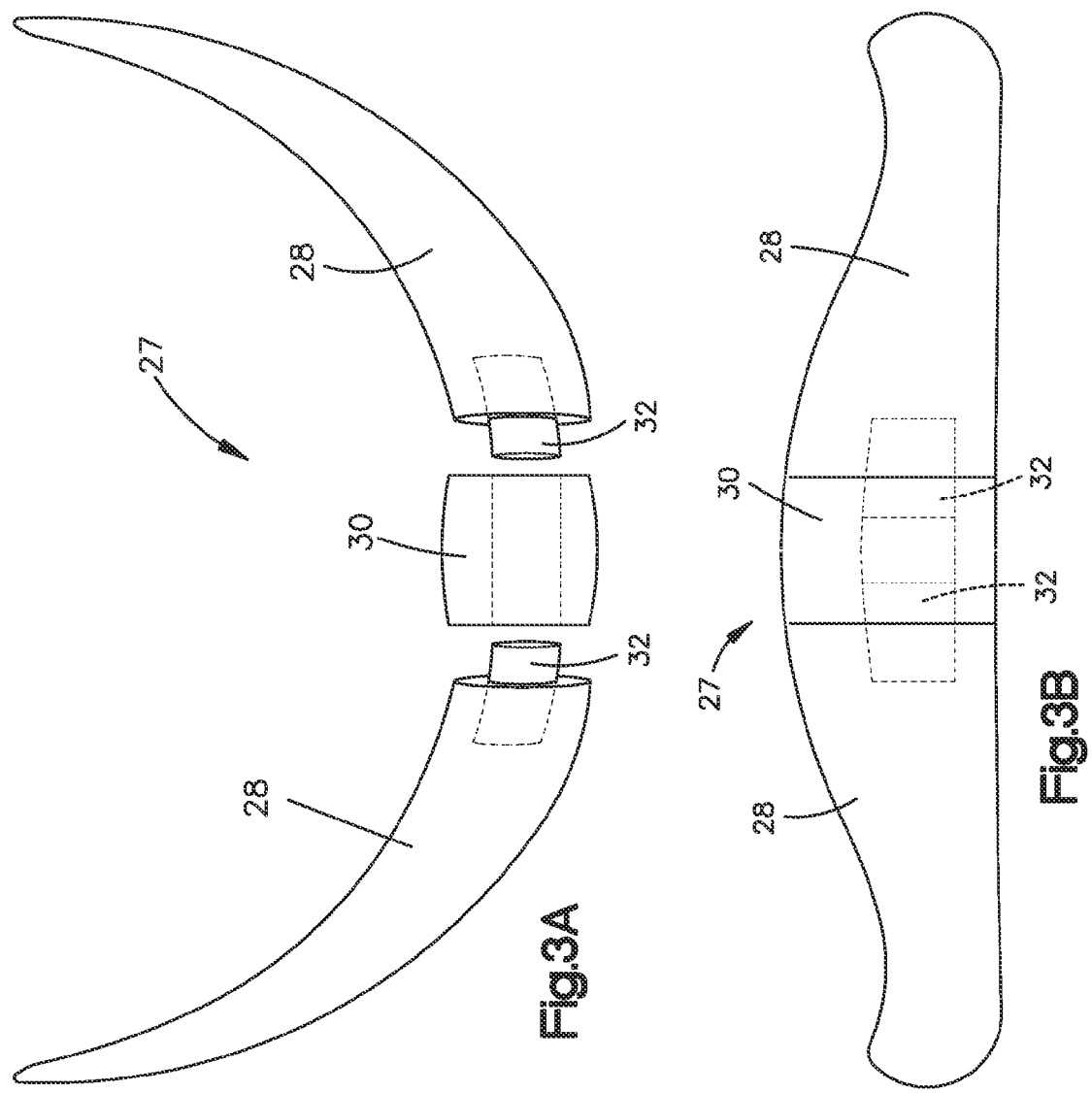

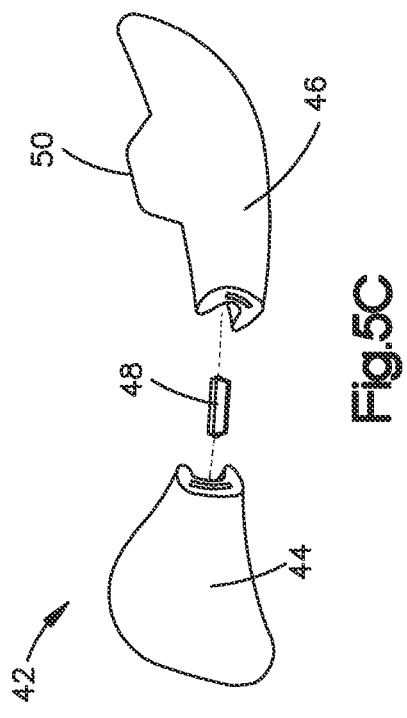
Fig.5C
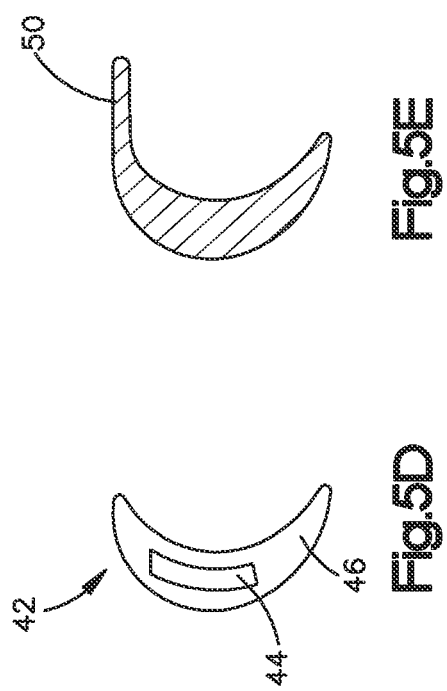
Fig.5E
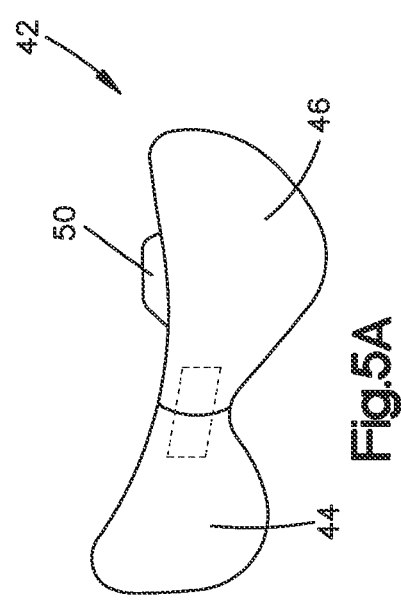
Fig.5A
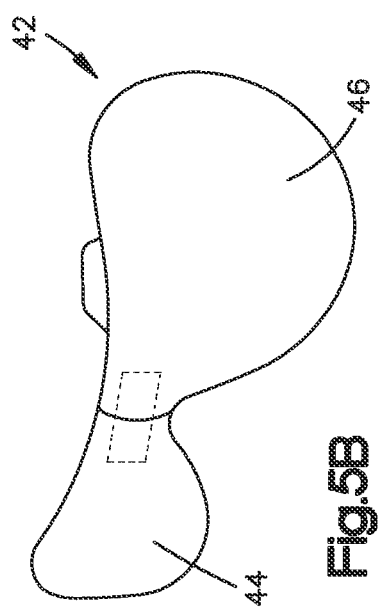
Fig.5B
Fig.5D

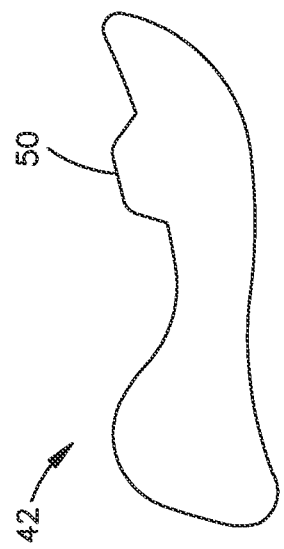
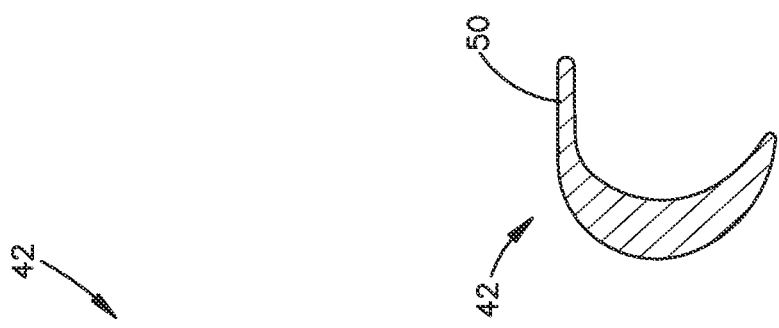
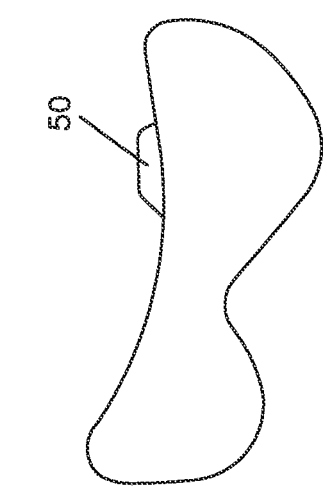

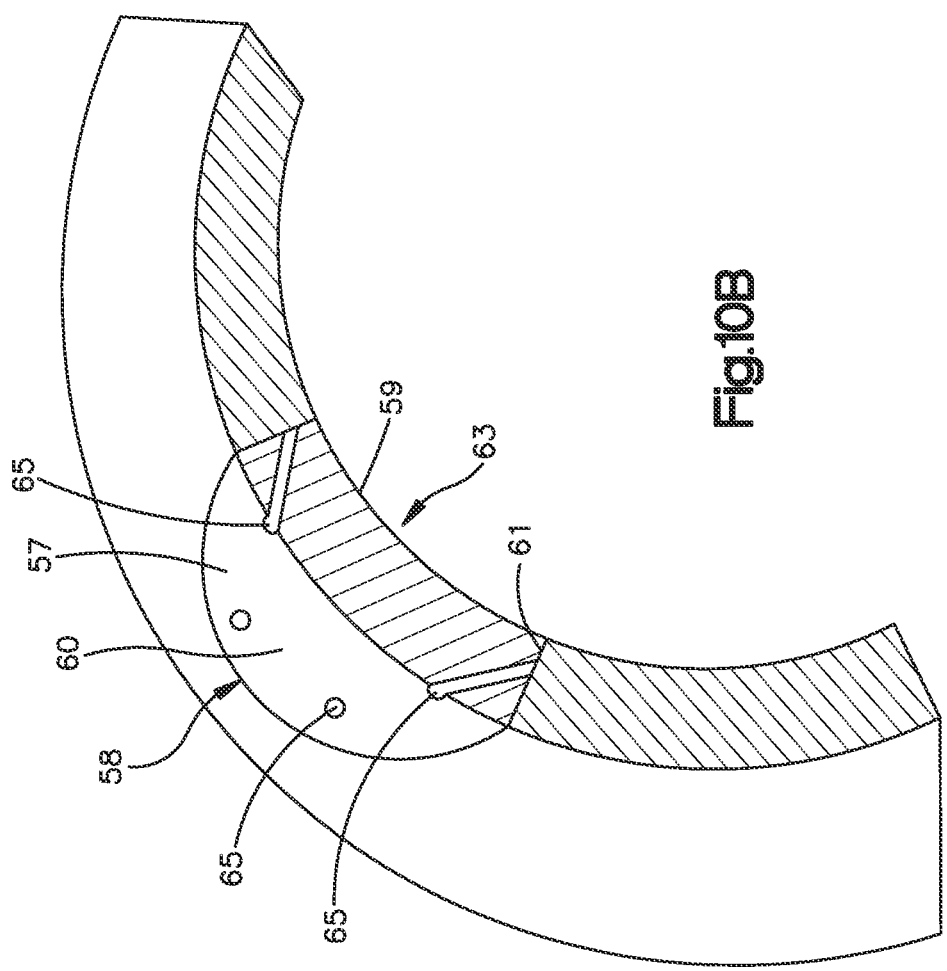

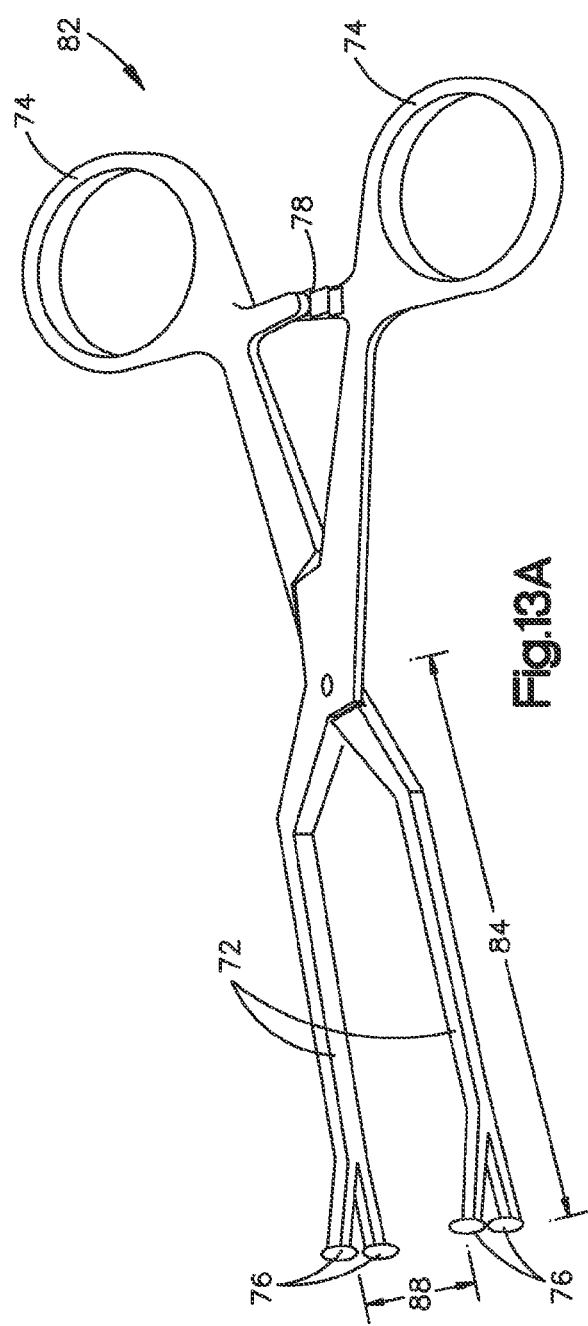
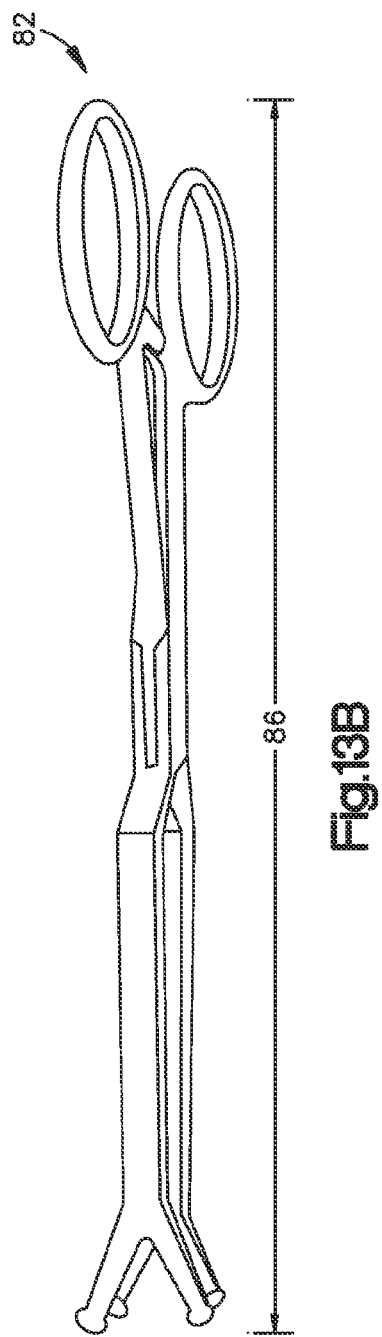

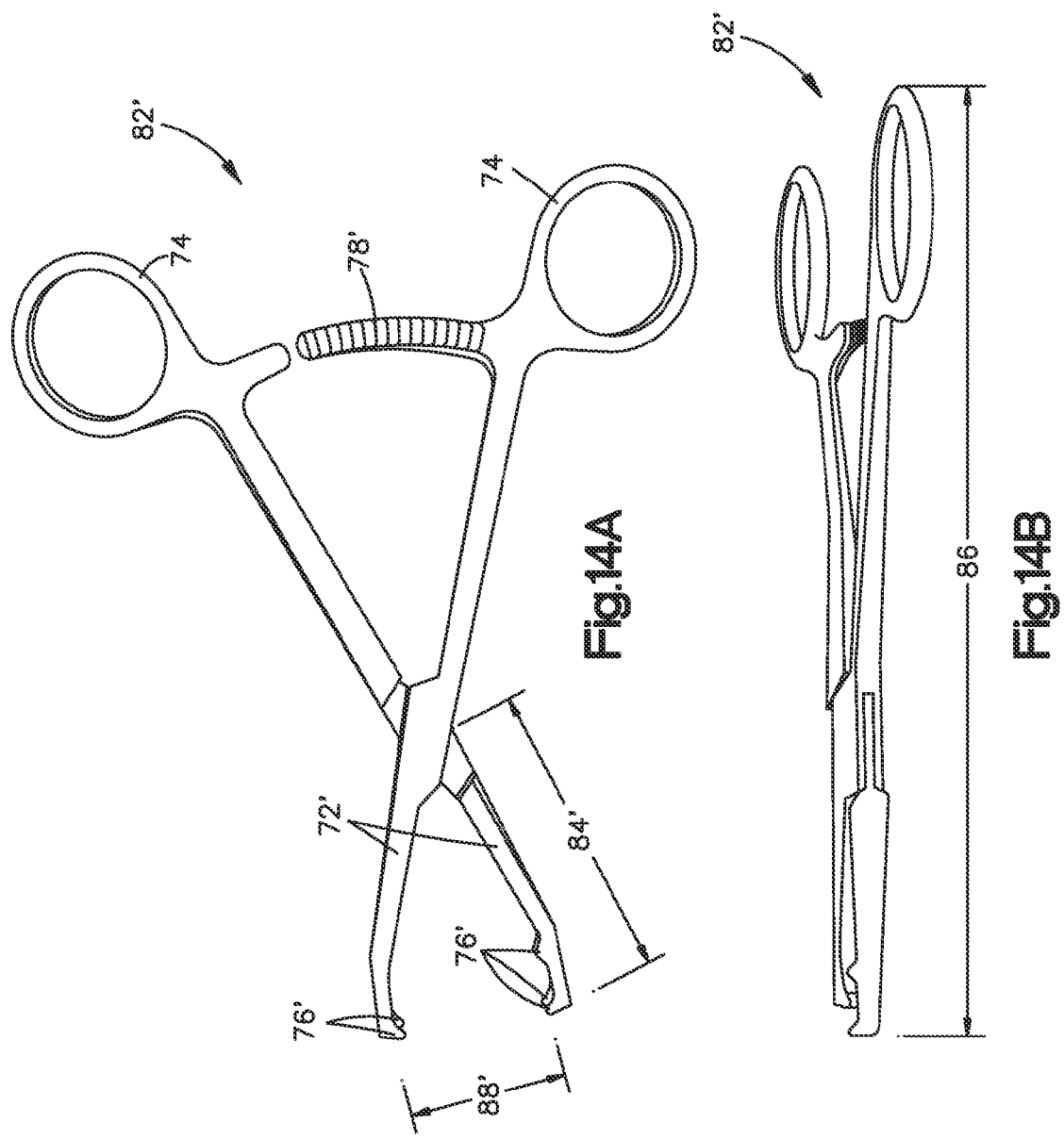

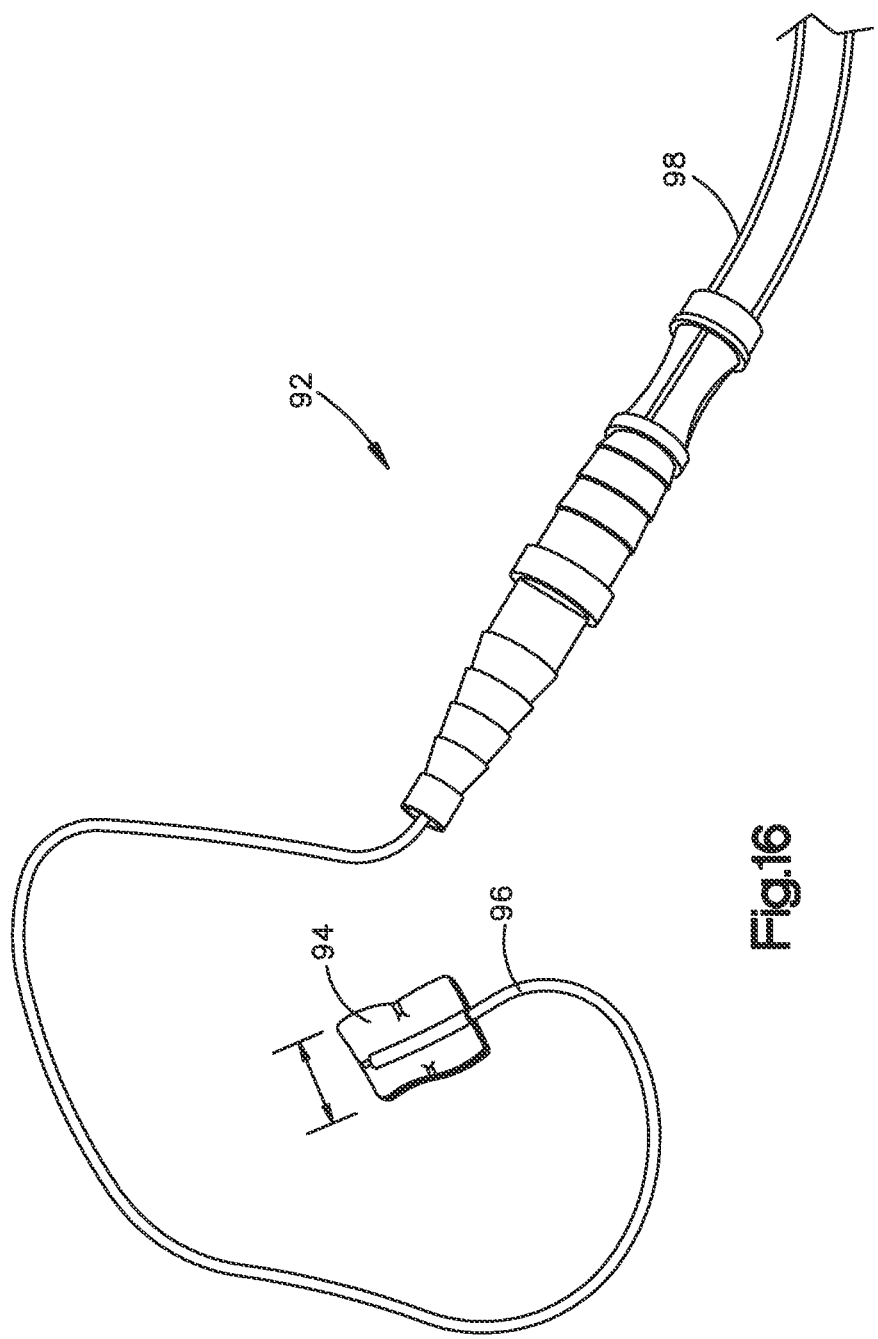

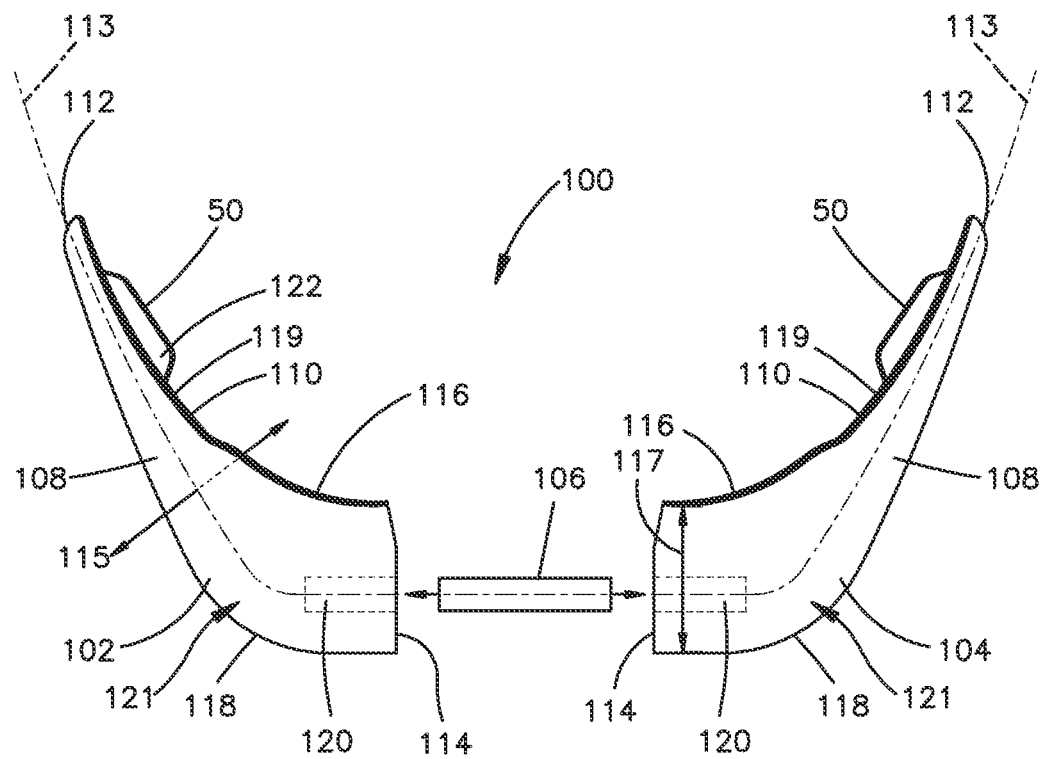
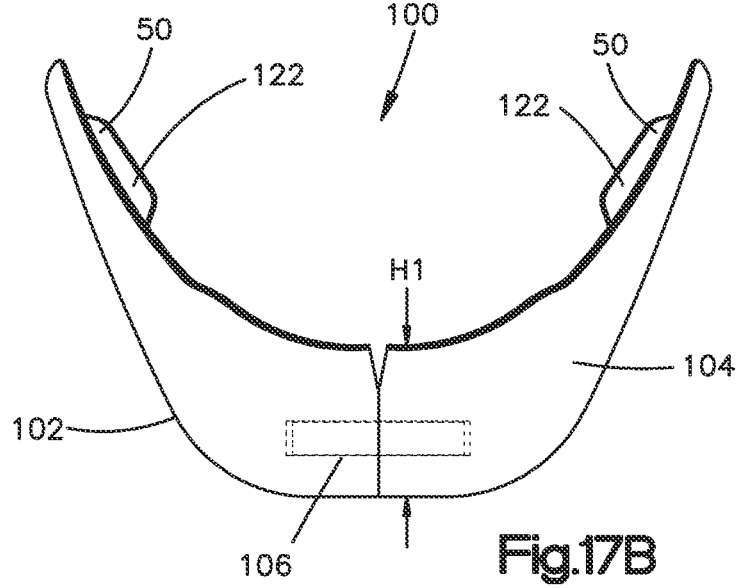

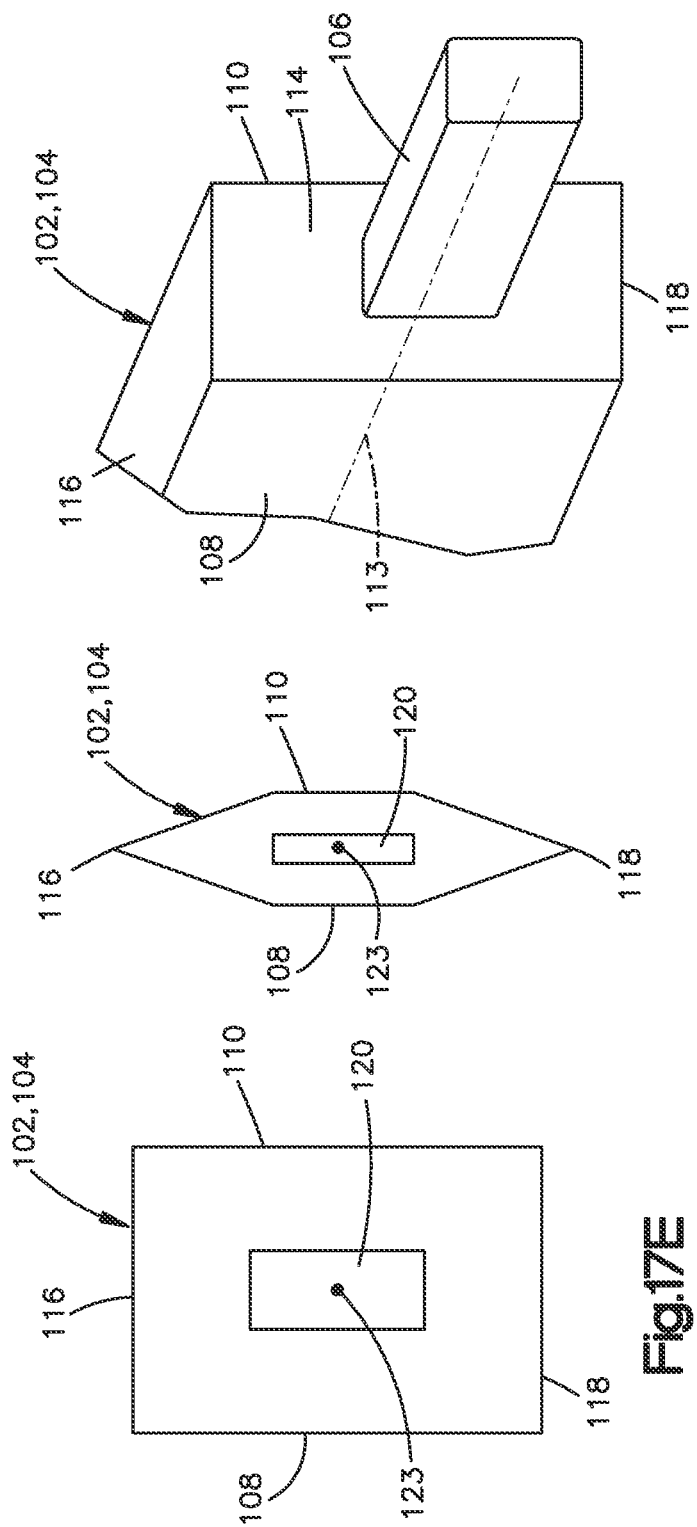

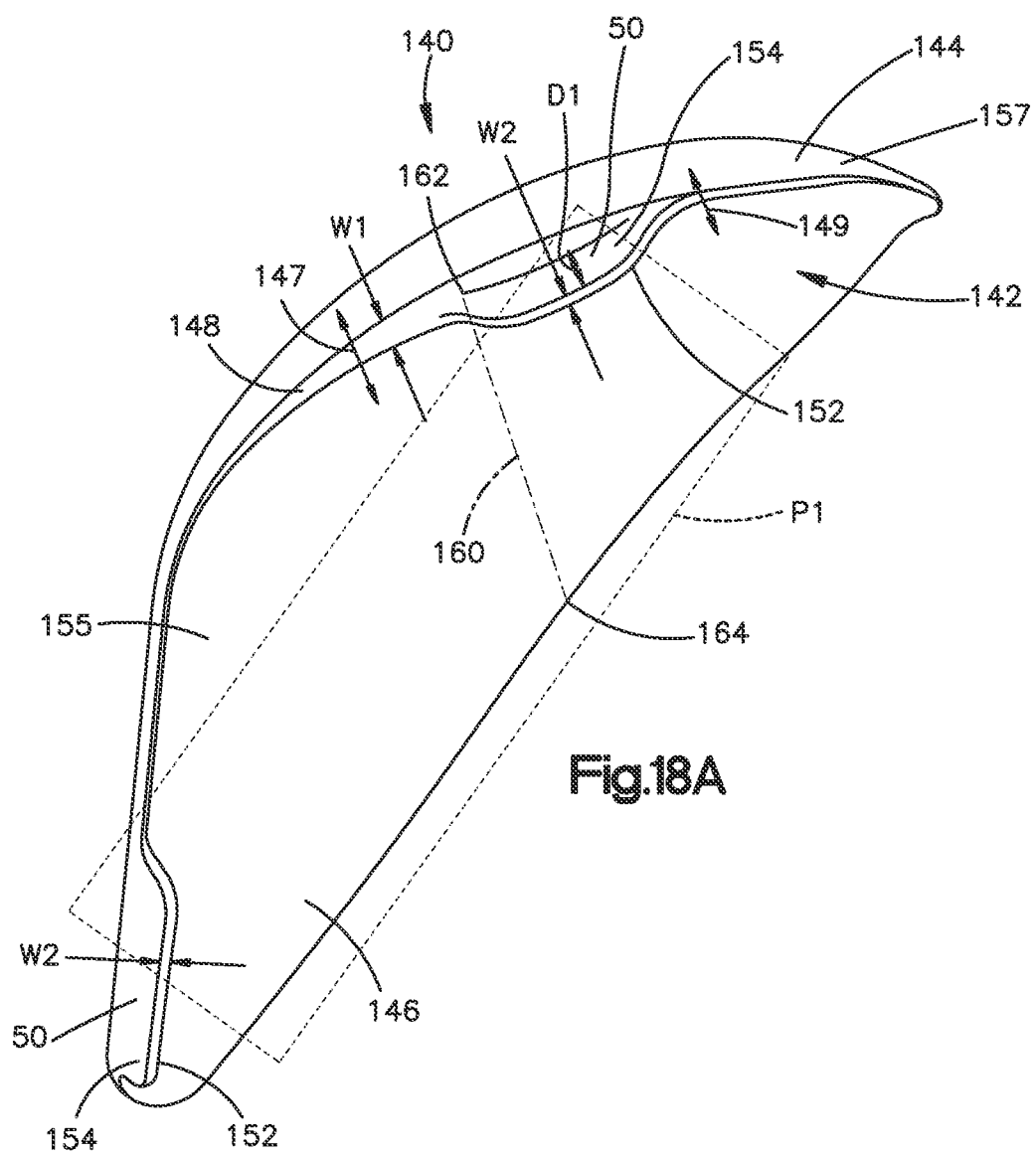

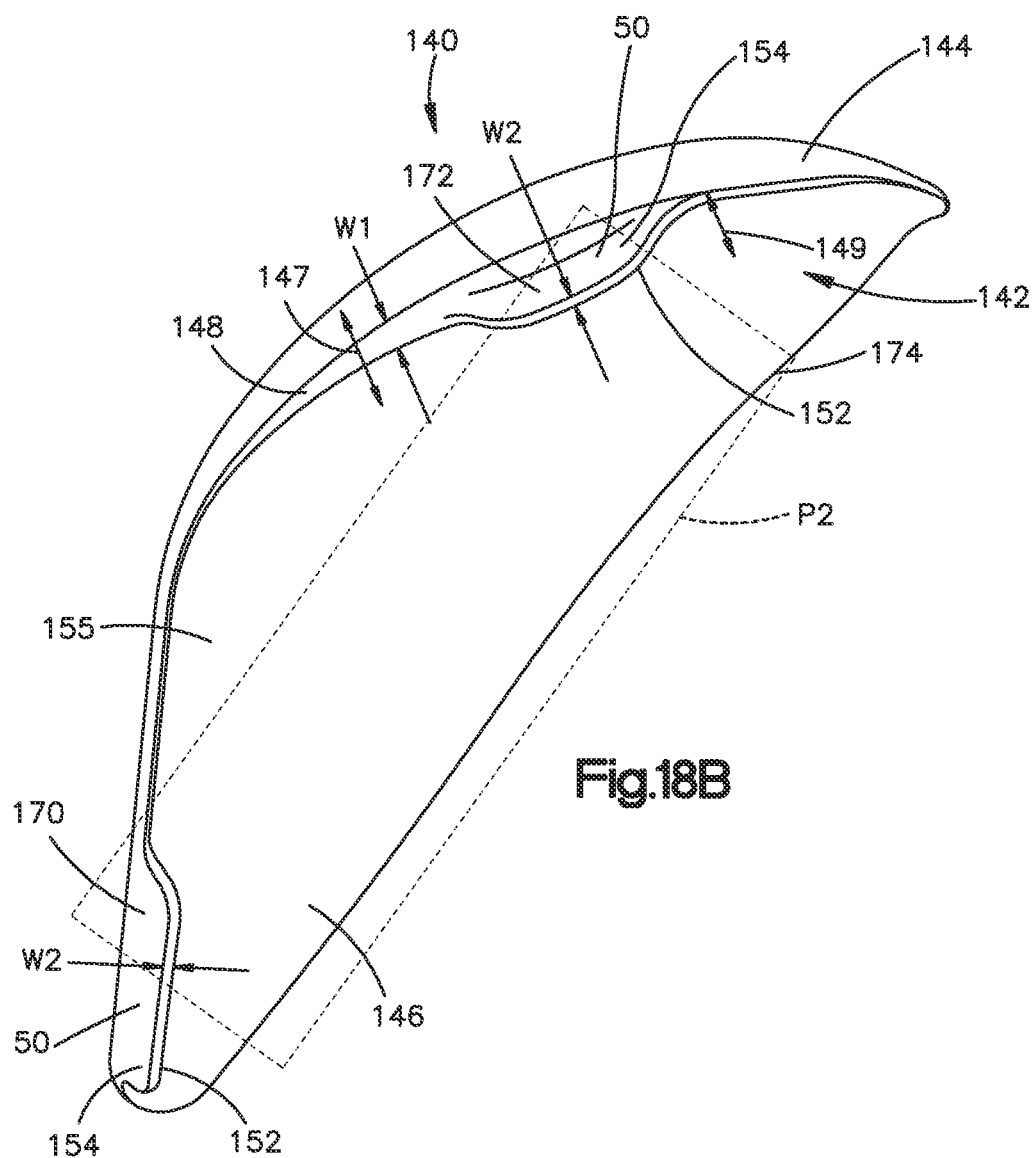

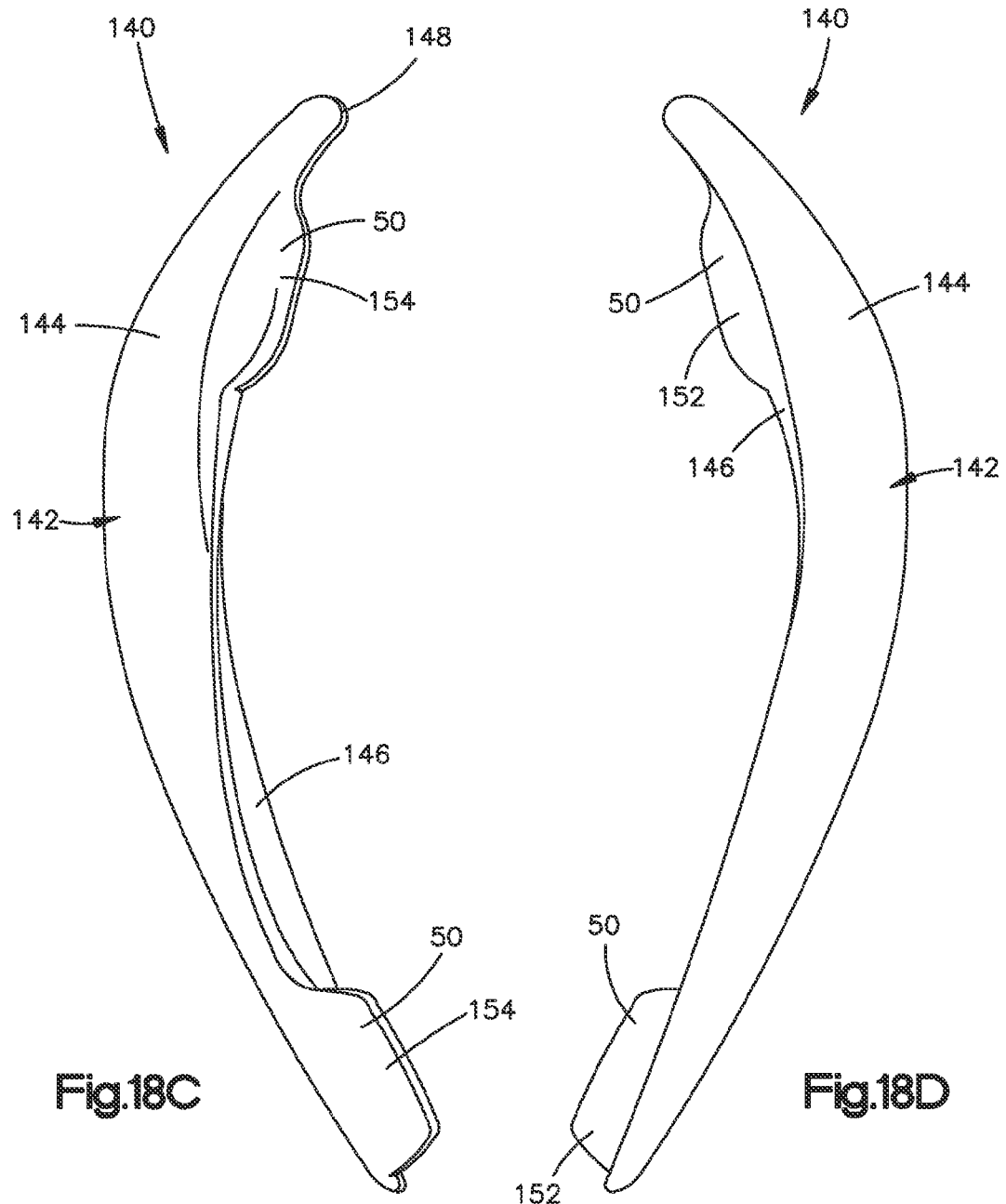

CRANIOFACIAL IMPLANT REGISTRATION FEATURES AND METHODS

CROSS REFERENCE TO RELATED APPLICATIONS

This patent application is a continuation-in-part of U.S. patent application Ser. No. 12/342,762 filed on Dec. 23, 2008 titled "Craniofacial Surgery Implant Systems and Methods", which claims the benefit of each of the following three provisional U.S. patent applications: U.S. Patent Application Ser. No. 61/018,943 filed Jan. 4, 2008, titled "Multi-Component Craniofacial Surgery Implant Systems and Methods"; U.S. Patent Application Ser. No. 61/018,948 filed Jan. 4, 2008, titled "Craniofacial Implant Registration Features and Methods"; and U.S. Patent Application Ser. No. 61/018,952 filed Jan. 4, 2008, titled "Craniofacial Implant Surgical Instruments and Methods". The subject matter of each of the above identified patent applications is hereby incorporated by reference as if set forth in its entirety herein.

TECHNICAL FIELD

The invention relates to surgical implants and more specifically to craniofacial implant systems and associated surgical methods employing multiple mating components and registration features on the implants. The invention further relates to surgical instruments and more specifically to craniofacial implant surgical instruments and associated surgical methods.

BACKGROUND

Craniofacial surgery is generally performed to treat congenital deformities of the face and facial skeleton, to treat traumatic injury, or to address cosmetic or aesthetic concerns of the patient. Skilled surgeons can enhance or reconstruct the facial skeleton using biocompatible implants that are disposed beneath the facial musculature and applied to or attached to the facial skeleton (typically using screw fasteners). For example, craniofacial surgery and biomaterials can be used to create new facial skeletal contours. See, for example, ATLAS OF FACIAL IMPLANTS (Elsevier, 2007) by Michael J. Yaremchuk, MD, the disclosure of which is incorporated herein by reference in its entirety. Unlike the use of injected liquid materials, that are meant to inflate the soft tissue envelope, the use of solid facial implants can mimic the facial appearance obtained with more extensive facial skeletal surgeries that require cutting and repositioning of facial bone. The facial implants are typically provided in a limited number of basic shapes, that can be carved and shaped by the surgeon at the time of implant.

Facial implants are conventionally made from silicone rubber or sintered porous plastics (such as polyethylene) that are molded into predetermined shapes, depending on the area of the face to be treated. See, for example, U.S. Pat. No. 6,551,608, the disclosure of which is incorporated herein by reference in its entirety. For each area, a family of implants of varying size and similar contour are often provided. This is required, so that the facial implants can be readily customized to suit both the underlying skeletal contours and the overlying facial tissue, in order to give the desired final appearance, without excessive sculpting of the implant by the surgeon during the implant procedure.

Problems can exist, however, due to the relatively large size of some of the implants (e.g., requiring more extensive surgical access to the area to be augmented) and/or the amount of customization and associated time required, due to the limited selection of implants in each family. In general, temporary size implants are often used intraoperatively to determine which implant shape might be appropriate, which requires a large inventory of implants to be available to the surgeon. Implants which are not optimal for the specific needs of the patient can sometime be used. Implants of different sizes must be custom carved and, in extreme cases, stacked and joined together by sutures if standard implants are not ideal for specific clinical situations. Alternatively, a shim can be custom cut and inserted underneath the implant and affixed thereto by protuberances and adhesive, as described in U.S. Pat. No. 5,514,179, the disclosure of which is incorporated herein by reference in its entirely. Current techniques can be inefficient and imprecise, and intraoperative constructs might be unstable in shape, leading to unpredictable outcomes. Further, the outcome can be less than ideal when the surgeon commits to opening an implant that, after placement, is less than ideal in projection.

The precise positioning of facial implants by the surgeon during the implant procedure is often difficult and time consuming, due to limited exposure of the areas to be augmented. Craniofacial implants are typically placed through remote access incisions to avoid visible scarring on the overlying soft tissue envelope and creation of suture lines directly over the implant which can predispose to wound breakdown, implant exposure and hence, surgical failure. Accurate implant placement is especially difficult when attempting to place a pair of implants symmetrically. For example, symmetric placement of facial implants can be problematic due to the complex three-dimension surface of the facial skeleton and limited surgical exposure.

In addition, placement of facial implants requires exposure (i.e., removal of overlying attached soft tissues) of the skeletal area to be augmented. Further, the implant needs to be held in proper position while it is being secured to the underlying bone, typically with screws. Available conventional clamps (e.g., tissue forceps, bone reduction forceps, towel clips, etc.) do not provide stable purchase of the implant and bone, due to their purchase end design, the dimensions of the purchasing end, and the configuration and orientation of the purchasing end. Inadvertent movement of the implant while it is being secured can result in implant malposition and, if recognized intraoperatively, the need to remove and reposition the implant.

SUMMARY

In one aspect, the present invention relates to craniofacial implants including a base implant and an optional onlay component that is contoured to the surface of the base implant allowing the overall projection of the implant to be adjustable.

In one embodiment, the craniofacial implant includes a base implant having an inner contoured surface adapted to conform to a boney structure and an outer contoured surface adapted to underlie soft tissue. The craniofacial implant also includes an optional onlay component having an inner contoured surface adapted to conform to at least a portion of the outer contoured surface of the base implant and an outer contoured surface adapted to underlie soft tissue, to adjust an overall projection of the implant. The craniofacial implant may include a means to attach the onlay component to the base implant. The means to attach the onlay component to the base implant can be a press fit, connecting tabs, a locking mechanism, or a registration feature. The base block and onlay component can include a biocompatible alloplastic material.

In another aspect, the invention relates to a craniofacial implant that includes a pair of substantially minor image implant components and an optional central segment to adjust the overall dimension of the implant. The craniofacial implant can include a pair of substantially mirror image implant components and an optional central segment adapted to be disposed therebetween and connected thereto, where the optional central segment can be selected from a group of segments having different dimensions in order to adjust the overall dimension of the implant. The craniofacial implant can include a means to attach the central segment to the implant components. The means to attach the central segment to the implant components can be a removable bar.

In another aspect, the invention relates to an adjustable elongation block implant including a base implant block having a substantially planar surface to conform to a surgically cut boney structure and an outer substantially planar opposed surface adapted to conform to an optional onlay block component and a mating surgically cut boney structure. The adjustable elongation block also includes an optional onlay block component having an inner substantially planar surface adapted to conform to the outer surface of the base implant block and an outer substantially planar opposed surface adapted to conform to at least one of an optional second onlay block component and a surgically cut boney structure, to fill a void formed by an osteotomy. The base block can be up to about 5 mm in height. The onlay component can be up to about 3 mm in height.

According to another aspect, the present invention relates to an infraorbital rim implant including a medial rim implant portion and a lateral malar implant portion that is selected from a group of at least two malar implants having at least one different dimension, to adjust an overall dimension of the implant. The infraorbital rim implant can include a means to attach the medial rim implant portion to the selected lateral malar implant portion. The means to attach the medial rim implant portion to the selected lateral malar implant portion can be a connecting extension bar. The infraorbital rim implant can be provided in a kit including a medial rim implant portion, at least two lateral malar implant portions having at least one different dimension, and a connecting extension bar.

In another aspect, the invention relates to craniofacial implants including an inner contoured surface adapted to conform to boney structure and an outer contoured surface adapted to underlie soft tissue, and a flange disposed along and extending from at least a portion of an edge thereof. The flange is adapted to abut a landmark feature of the boney structure, to position initially the implant along at least one dimension. The craniofacial implant can be designed to augment periorbital, midface and mandible surfaces (e.g. infraorbital rim implants, mandible implants, and paranasal implants). The flange can be positioned to abut the landmark feature selected from the group consisting of a lateral aspect of an orbital floor or wall, an aspect of the zygomatic arch, an inferior border of a mandible body or chin, a posterior border of a mandible ramus, and a pyriform aperture. When included on a mandible implant, the flange can be configured to allow accurate and stable placement with minimal manipulation and disruption of the pterygomasseteric sling.

Another aspect of the invention relates to a horizontal or a sagittal osteotomy implant including a flat surface adapted to lay on an anterior face of each of a pair of relatively repositioned bones and a positioning ledge adapted to wrap around an inferior border of each of these bones to restore or create a continuous lower border.

Yet another aspect of the invention relates to a cranial implant comprising a cranial body portion adapted to substantially fill a cranial defect and a cranial thin edge portion of a periphery thereof that is adapted to receive fasteners to attach the implant to the cranium. The periphery of the cranial thin edge portion can include openings, for instance through holes, that are configured to receive the fasteners to attach the implant to the cranium. In one embodiment, the through holes can be predrilled prior to insertion of the implant. The fasteners can be chosen based on their length. In one embodiment a CT scan can be used to determine a thickness of the cranium that the implant is being attached to. The fastener can then be selected based on the thickness of the cranium such that the insertion of the fastener does not increase the implant profile. The thin edge portion can include a taper. The taper can be from about 1.5 mm to less than 1 mm. The cranial implant may further include an intracranial inner cup having a convex surface adapted to a brain and an edge portion along at least a portion of a periphery thereof adapted to receive therethrough fasteners. The intracranial inner cup can be adapted to attach to at least one of the cranial body portion and the cranial thin edge portion, or the cranial body portion.

Still another aspect of the invention relates to surgical instruments for manipulating a craniofacial implant including a pair of pivoting jaws connected to a respective pair of finger grips, where each jaw includes spaced lobes to provide contact and preclude substantially relative movement of a craniofacial implant disposed therebetween. The surgical instrument also includes a locking mechanism disposed between the finer grips to retain the finger grips in at least one predetermined relative spacing corresponding to a nominal jaw opening. The pivoting jaw can include a pair of spaced lobes or three spaced lobes. The locking mechanism can include a ratchet system. The nominal jaw opening can have a value in the range of about 1 mm to about 10 mm when the locking mechanism is engaged. The jaws can be adapted to grasp a craniofacial implant therebetween. The nominal jaw opening can have a value in a range of about 10 mm to about 50 mm when the locking mechanism is engaged. The jaws can be adapted to clamp a craniofacial implant to bone. The pivoting jaws can be adapted to open a distance of up to about 4 mm. The distance from the lobes to the pivoting point can be up to about 70 mm. The overall instrument length can be up to about 140 mm. The pivoting jaws can be adapted to pen a distance of up to about 20 mm. The distance from the lobes to the pivoting point can be up to about 60 mm. The overall instrument length can be up to about 100 mm.

The invention also relates to a facial implant instrumentation system including various components, such as a straight periosteal elevator, a curved periosteal elevator, a cutting board with a grid system, at least one surgical instrument described above, a 1.5 mm hand drill, a sterile battery powered micro drill system allowing for a sleeve system for placement of non-sterile batteries into the battery powered micro drill, a 2.0 mm selection of screws, a screw driver, a suction drain with trocar, and an evacuation patty in various combinations. The facial implant instrumentation system includes a selection of screws, a screw driver, at least one surgical instrument described above, and at least one sterile batter powered micro drill and an evacuation patty.

BRIEF DESCRIPTION OF THE DRAWINGS

The objects and features of various aspects and embodiments of the invention can be better understood with reference to the schematic drawings described below, and the claims. The drawings are not necessarily to scale, emphasis instead generally being placed upon illustrating the principles of the invention. In the drawings, like numerals are used to indicate like parts throughout the various views. In the drawings:

FIG. 3A is a top view of a craniofacial implant including a pair of mirror image base implant components and an optional central base segment in accordance with one embodiment of the invention;

FIG. 3B is a frontal view of the craniofacial implant of FIG. 3A;

FIG. 5A is a frontal view of an infraorbital rim implant in accordance with one embodiment of the invention;

FIG. 5B is a frontal view of the infraorbital rim implant of FIG. 5A with a different size lateral malar implant portion;

FIG. 5C is an exploded view of the infraorbital rim implant of FIG. 5A;

FIG. 5D is a lateral end view of a portion of the infraorbital rim implant of FIG. 5A;

FIG. 5E is a cross-sectional view of a portion of the infraorbital rim implant of FIG. 5A;

FIG. 6A is a frontal view of an infraorbital rim implant with a flange in accordance with one embodiment of the invention;

FIG. 6B is a top view of the infraorbital rim implant of FIG. 6A;

FIG. 6C is a lateral cross-sectional view of the infraorbital rim implant of FIG. 6A;

FIG. 10B is a depiction of a cranial implant in accordance with another embodiment;

FIG. 13A is a top perspective view of an implant positioning clamp in accordance with one embodiment of the invention;

FIG. 13B is a side view of the implant positioning clamp of FIG. 13A;

FIG. 14A is a top view of an implant positioning clamp in accordance with one embodiment of the invention having multiple lobes;

FIG. 14B is a side view of the implant of FIG. 14A;

FIG. 16 is a schematic plan view of an evacuation patty in the system of FIG. 15 in accordance with one embodiment of the invention;

FIG. 17A is a frontal view of a mandible implant according to another embodiment in an unassembled configuration, the mandible implant including a first and second body portions and a joining element configured to attach to the first and second body portions;

FIG. 17B is a frontal view of the mandible implant illustrated in FIG. 17A in an assembled configuration, the mandible implant including the connecting bar shown in dotted lines positioned within the pair of base implant components;

FIG. 17E is an end elevation view of the base implant components illustrated in FIG. 17A;

FIG. 17E is an end elevation view of the base implant components illustrated in FIG. 17A, but constructed in accordance with an alternative embodiment;

FIG. 17G is a perspective view of an end of the first body portion of the mandible implant illustrated in FIG. 1, but constructed in accordance with an alternative embodiment showing the joining element integral with one of the first and second body portions;

FIG. 18A is a perspective view of a malar implant according to one embodiment;

FIG. 18B is a perspective view of a malar implant according to another embodiment;

FIG. 18C is a top view of the malar implant illustrated in FIG. 18A;

FIG. 18D is a bottom view of the malar implant illustrated in FIG. 18A.

DETAILED DESCRIPTION OF ILLUSTRATIVE EMBODIMENTS

According to various embodiments of this invention, implants can be made in multiple mating pieces to reduce the inventory of implants required, while providing a high level of customization with limited sculpting or custom shimming by the surgeon during the implant procedure. While porous polyethylene material may be used, the invention is not limited in this regard and any suitable biocompatible material may be employed (e.g., rigid or flexible, porous or nonporous, polymer or nonpolymer, etc.). The implants of the present invention may be provided in kit form with or without fasteners and/or conventional or specialized surgical instruments described herein.

Figure 1A:
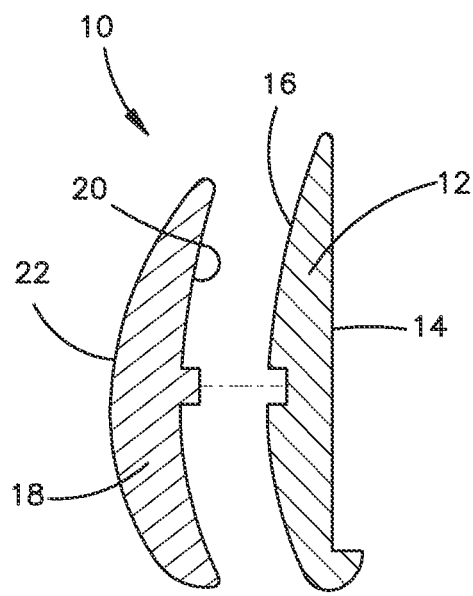
FIG. 1A is a schematic cross-sectional view of an adjustable size craniofacial implant in accordance with one embodiment of the invention.
Figure 1B:
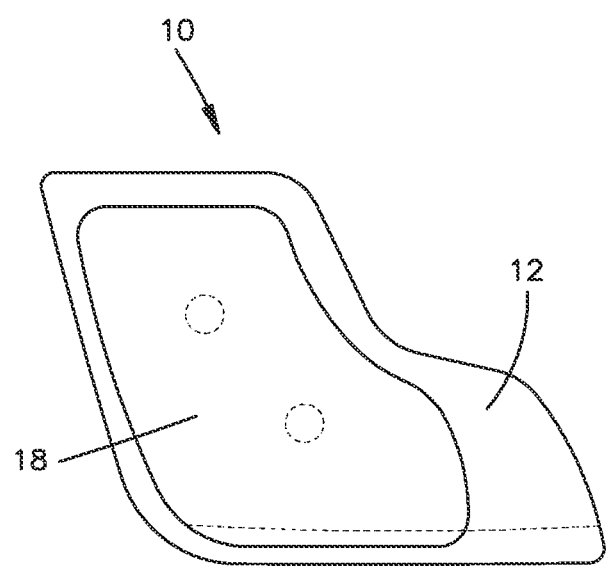
FIG. 1B is a lateral view of the adjustable size craniofacial implant of FIG. 1A.
Figure 1C:
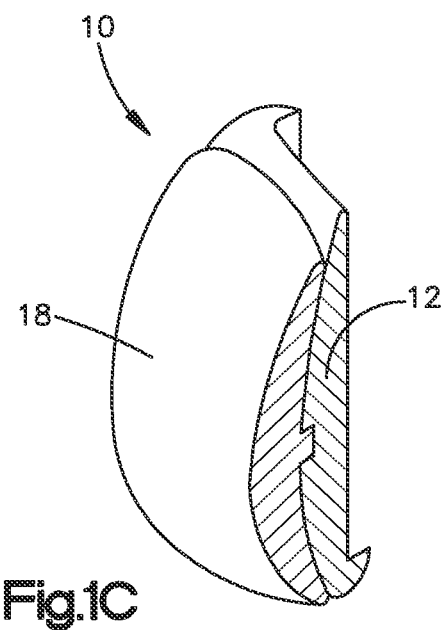
FIG. 1C is a front oblique cross-sectional view of the adjustable size craniofacial implant of FIG. 1A.

A first embodiment, an example of which is shown in FIG. 1, provides implants with adjustable projection. A two or more piece layered configuration provides controlled variability in the amount of augmentation provided by a single implant. In general, this embodiment relates to a craniofacial implant 10 including a base implant 12 having an inner base contoured surface 14 adapted to conform to a boney structure and an outer base contoured surface 16 adapted to underlie soft tissue. The craniofacial implant 10 further includes an optional onlay component 18 having an inner onlay contoured surface 20 adapted to conform to at least a portion of the outer base contoured surface 16 and an outer onlay contoured surface 22 adapted to underlie soft tissue, to adjust an overall projection of the implant. The craniofacial implant 10 further includes a means 19 to attach the onlay component 18 to the base implant 12.

In general, the craniofacial implant 10 consists of at least two pieces. The base implant 12 may be of variable shape and dimensions appropriate to augment the skeletal area of perceived deficiency. A second onlay component 18 mimics the outer shape of the base implant 12. The posterior contoured surface 20 of the onlay component 18 is congruent with the mating contoured undersurface 16 of the base implant 12. The onlay component 18 can be attached to the base implant by a press fit, connecting tabs, sutures, or other registration and interlock features known in the art. Plugs or other suitable fillers can be used to conform exposed depressions in the outermost contoured surface base implant 12 or only component 18, as necessary. Biocompatible adhesives may be used alone or in combination with the mechanical attachment schemes. The surgeon can use either the base implant 12 or the base implant 12 and the onlay component 18 together, as appropriate. Each optional third and subsequent onlay component mimics the outer shape of the underlying implant piece.

This embodiment of the invention allows for selectability in the amount of augmentation provided by a single implant, which can be useful in cases of facial asymmetry. The selectability is also useful when the surgeon is unsure initially as to the appropriate amount of augmentation. The implant with and without its onlay component can be evaluated intraoperatively. Thus, a single implant provides options in the amount of augmentation and decreases inventory requirements for the surgeon, operating facility, and implant manufacturer.

Figure 2A:
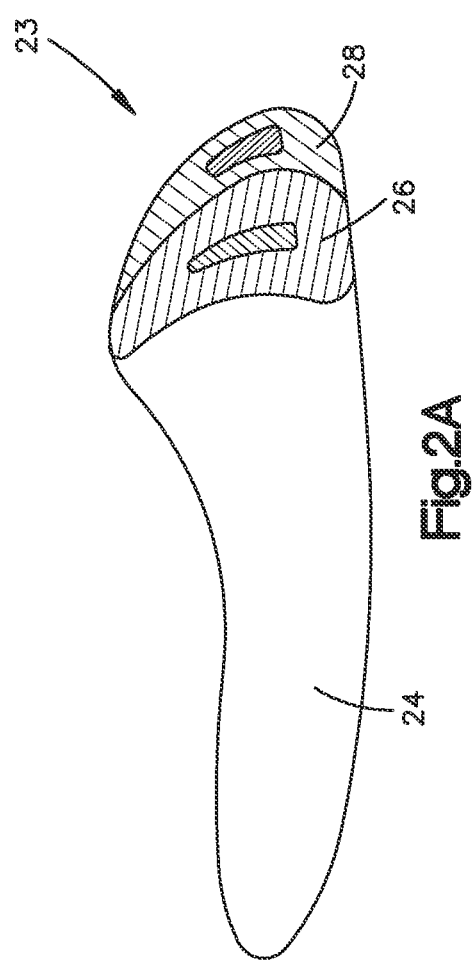
FIG. 2A is a medial cross-sectional view of an adjustable mandible chin implant in accordance with one embodiment of the invention.
Figure 2B:
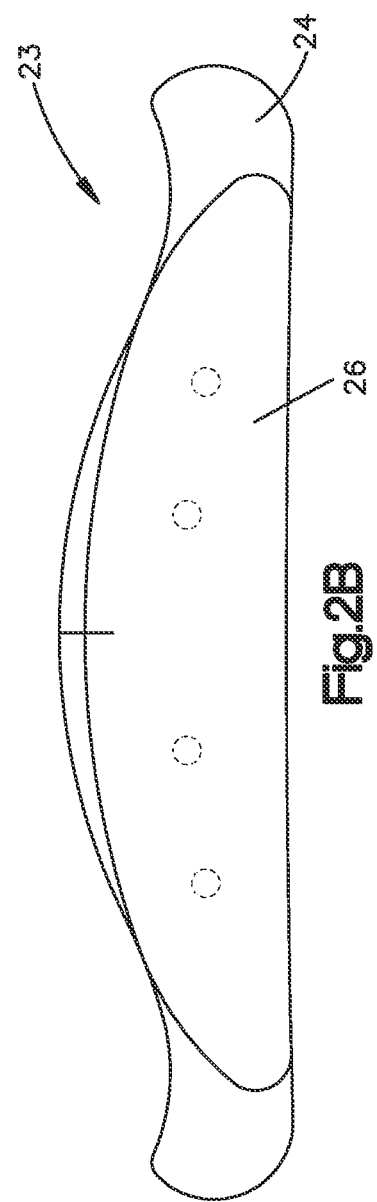
FIG. 2B is a frontal view of the adjustable mandible chin implant of FIG. 2A.

In another embodiment, an adjustable size mandible chin implant 23 (see FIG. 2A-2B) or an adjustable chin implant 27 can be provided (see FIG. 3A-3B). The configuration of the mandible base implant 24 for the mandible angle may be such that it provides up to about 6 mm or more of lateral augmentation and its optional mandible onlay component 26 provides up to about an additional 4 mm or more. Similarly, the adjustable chin implant 27 can provide up to about 5 mm or more projection base implant, with an optional mandible onlay component 26 having an additional up to about 3 mm or more projection. Additionally, due to the size of the adjustable chin implant 27, it can be made in two halves, to facilitate insertion with minimal incision size. Similar onlay components (in any number of layers) can be configured for malar, chin, and nasal dorsum implant regions.

Moreover, the adjustable chin implant 27 can optionally be configured as a three segment implant, designed to augment the contours of the chin. This embodiment of the invention, alone or in combination with the adjustable projection feature, relates to a craniofacial implant including a pair of substantially mirror image base implant components 28 and an optional central base segment 30 adapted to be disposed therebetween and connected thereto, the optional central base segment 30 selected from a group of segments having at least one different dimension, to adjust an overall dimension of the implant. The adjustable chin implant 27 further comprises means to attach the central segment to the implant components.

Conventional chin implants consist of a single piece of material of certain dimensions or two pieces joined at the center. The inclination of the lateral limbs of the implant often do not mimic the inclination of the inferior border of the mandible resulting in failure of the implant to appropriately augment the inferior border. Moreover, a fixed central width may be inappropriate for a particular patient.

Minor image base implant components 28 of this embodiment of the invention allow the inferior border of the implant to be congruent with the inferior border of the mandible, and the central base segment 30 allows flexibility in control of the width and, therefore, shape of the chin. Thus, right and left limbs allow the inferior border of the implant to be congruent with the inferior border of any mandible. This advantageous feature of this embodiment of the invention is not possible with standard one piece implants. The central base segment 30, which can be contoured and sized to any width, allows adjustment of the width of the chin Removable bars 32 or other structures can be used to connect the segments of the implant. The bars 32 fit into slots in each segment of the adjustable chin implant 27. The bars 32 can be attached to the mirror image base implant components 28 by a press fit, connecting tabs, sutures, or other registration and interlock features. The bars 32 may, alternatively, be integrally formed with either the central base segment 30 or with the mirror image base implant components 28. Biocompatible adhesives may be used alone or in combination with the mechanical attachment schemes.

The adjustable chin implant 27 allows greater clinical application of a single implant design. For example, a petite female requiring 5 mm of sagittal projection may be best served with a 5 mm adjustable chin implant 27 without a central base segment 30; whereas, a male requiring 5 mm of sagittal projection may be best served with a 5 mm adjustable chin implant 27 with half of the central base segment 30. Alternatively, a male requiring 5 mm of sagittal projection and a square chin may be best served with a 5 mm adjustable chin implant 27 with the entire central base segment 30. The three piece design provides controlled variability in the amount of central width provided by a single implant. Thus, the single adjustable chin implant 27 provides options in the amount of augmentation and decreases inventory requirements for the surgeon, operating facility, and implant manufacturer.

Figure 4A:
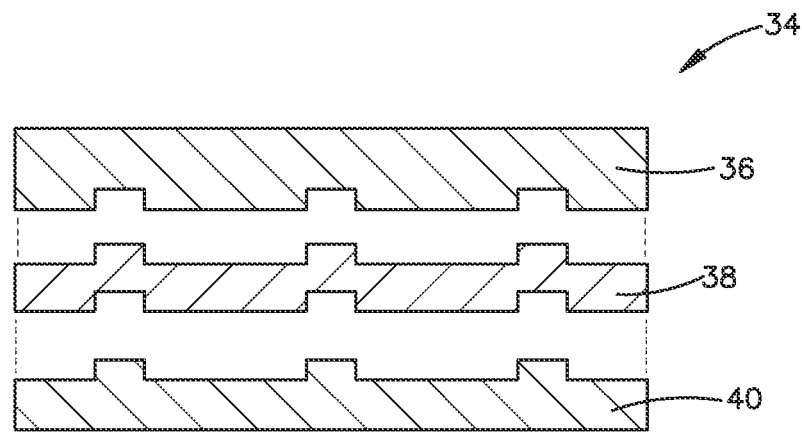
FIG. 4A is a top cross-sectional view of an adjustable elongation block implant in accordance with one embodiment of the invention.
Figure 4B:
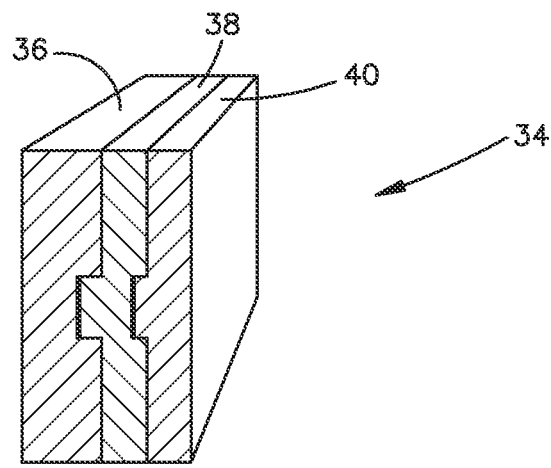
FIG. 4B is a cross-sectional side view of the adjustable elongation block implant of FIG. 4A.
Figure 4C:
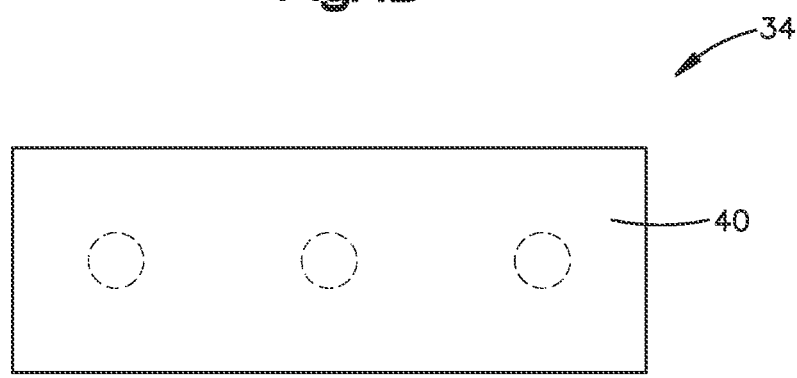
FIG. 4C is a frontal view of the adjustable elongation block implant of FIG. 4A.

Another embodiment of the invention provides an adjustable elongation block implant 34, configured to fill the space resulting from a chin osteotomy after vertical or sagittal advancement. The adjustable elongation block 34 can be used to correct deformities or to restore the original contour of the underlying bony structure. In general, this embodiment of the invention relates to a chin osteotomy implant including a base elongation implant block 36 having an inner substantially planar surface adapted to conform to a surgically cut boney structure and an outer substantially planar opposed surface adapted to conform to at least one of an optional onlay elongation block component 38 and a mating surgically cut boney structure, and the optional onlay elongation block component 38 having an inner substantially planar surface adapted to conform to the outer surface of the base elongation implant block 36 and an outer substantially planar opposed surface adapted to conform to at least one of an optional second onlay elongation block component 40 and a surgically cut boney structure, to fill a void formed by osteotomy. The implant further includes means to attach the optional onlay elongation block component 38 to the base elongation implant block 36. One example of this embodiment is depicted in FIGS. 4A-4C.

More specifically, a horizontal osteotomy performed to vertically elongate the mandible typically leaves a gap between the mandible proper and the mobilized chin segment. This gap makes the lowered chin position unstable. The chin osteotomy adjustable elongation block implant 34 is adapted to fill this space. The adjustable elongation block implant 34 can be made of any strong material, such as a biocompatible alloplastic material. In this embodiment the adjustable elongation block implant 34 consists of a base elongation implant block 36 up to about 5 mm in height or more. Onlay elongation block components 38 of up to about 3 mm or more in height can be press fit to allow adjustment of the chin height. The adjustable elongation block implant 34 allows the space between the bone segments to be precisely controlled and maintained at these intervals. A final elongation block component 40 can cap the adjustable elongation block implant 34. The bone segments are then immobilized with the surgeon's desired fixation technique (e.g., plates and screws). The adjustable elongation block implant 34 is suitable whenever a surgeon performs a vertical elongation of the chin after horizontal osteotomy. Naturally, the onlay elongation block components 38 can be of the same or different heights and need not be rectangular in shape.

The adjustable elongation block implant 34 allows precise maintenance of the desired distance between the osteotomized segment and the mandible proper and hence, chin height. It eliminates the potential for any asymmetries at either end of the osteotomy, by filling the resultant void after osteotomy and elongation resulting instability of the movement. The adjustable elongation block implant 34 also lessens space available for hematoma accumulation and eliminates the need for bone grafts (with accompanied donor site morbidity) or use of bone substitutes that may not provide sufficient rigidity. The need to create spacers, custom-carved from for example, large polyethylene blocks, is also eliminated. The use of the elongation block implant 34 provides for more efficient, precise and predictable surgery. Further, the adjustable nature of the elongation block implant 34 allows intraoperative adjustment without penalty of opening another implant.

Another embodiment of the invention depicted in FIGS. 5A-5E, relates to an infraorbital rim implant 42, typically used to treat congenital or post-traumatic upper midface concavity, relative upper midface deficiency after Lefort I lower maxillary advancement, as well as senescent upper midface deficiency as part of facial rejuvenation procedures. The complex configuration of the infraorbital rim and limited surgical access make placement of a conventional implant tedious and adaption to the underlying skeleton difficult. This embodiment of the infraorbital rim implant 42 includes a medial rim implant portion 44 and a lateral malar implant portion 46 selected from a group of at least two malar implants having at least one different dimension, to adjust an overall dimension of the implant. The infraorbital rim implant 42 further includes means to attach the medial rim implant portion 44 to the selected lateral malar implant portion 46.

In one embodiment, the means of attaching the lateral malar implant portion 46 and medial rim implant portion 44 is a connecting extension bar 48 joining the two halves of the infraorbital rim implant 42. The extension bar allows the infraorbital rim implant 42 to be placed as two separate halves. The connecting extension bar 48 also gives the infraorbital rim implant 42 flexibility, effectively allowing the implant to hinge to better conform to the underlying skeleton. The lateral malar implant portion 46 can include a larger malar option piece 46' similar to lateral malar implant portion 46 to allow it to cover more of the malar aspect in addition to the medial rim implant portion 44. See FIG. 5B. As with the adjustable chin implant 27 described above, the connecting extension bar 48 fits into slots in each half. The connecting extension bar 48 can be attached to each half by a press fit, connecting tabs, sutures, or other registration and interlock features known in the art. The connecting extension bar 48 may, alternatively, be integrally formed with either half, for example, with titanium wire or mesh. Biocompatible adhesives may be used alone or in combination with the mechanical attachment schemes. This aspect of the invention also presents an implant kit including a consistent medial rim implant portion 44 and two or more possible lateral malar implant portions 46, along with the connecting extension bar 48.

The infraorbital rim implant 42 design facilitates implant placement and positioning. It allows the infraorbital rim implant 42 to fit flush on the underlying skeleton and the adjacent anterior malar area to be augmented in a seamless, coordinated way. This improvement eliminates the need to modify existing implants, for example by cutting into pieces to allow placement and conformability. This improvement also eliminates the need to overlay a separate malar implant over the rim implant, if the malar area also requires augmentation. This improvement prevents inaccurate reassembly of segmented implants, and difficulties associated with placement of secondary malar implants over primary rim implants.

Figure 7A:
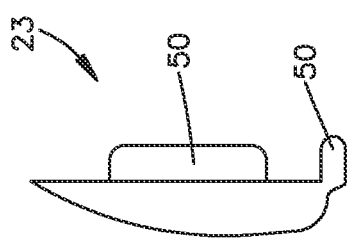
FIG. 7A is a side view of a mandible implant with flanges in accordance with one embodiment of the invention.
Figure 7C:
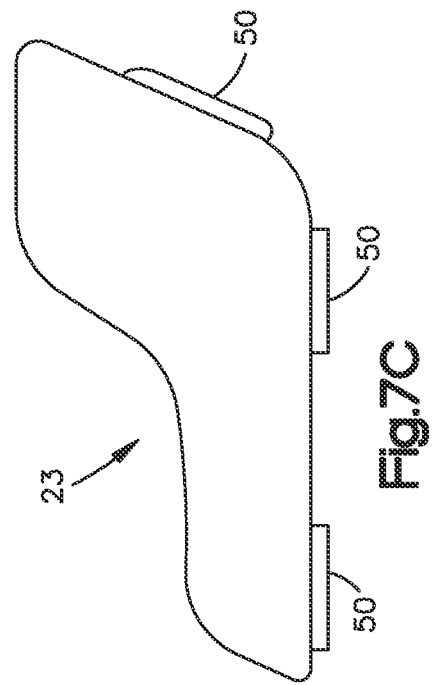
FIG. 7C is a medial view of the mandible implant of FIG. 7A.
Figure 7B:
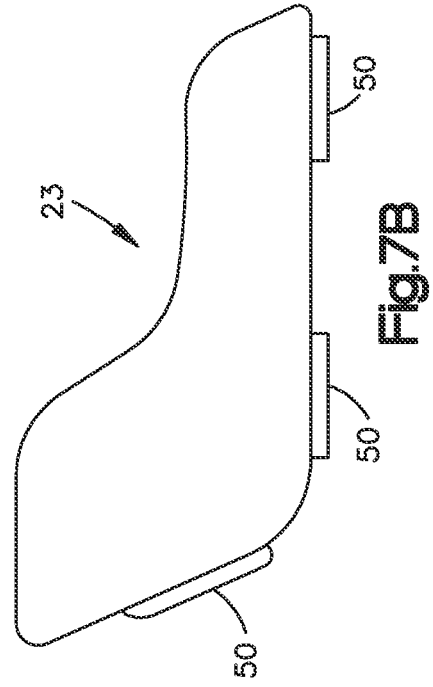
FIG. 7B is a lateral view of the mandible implant of FIG. 7A.
Figure 8A:
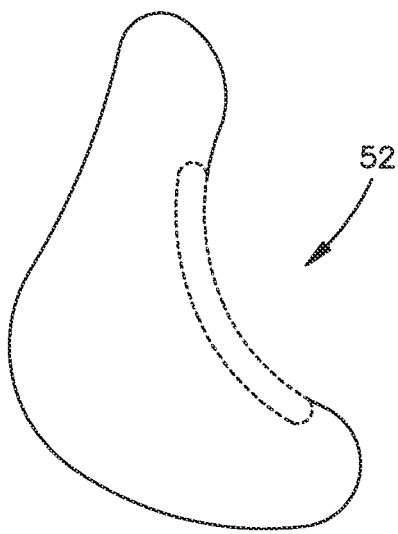
FIG. 8A is a lateral view of a paranasal implant with flanges in accordance with one embodiment of the invention.
Figure 8B:
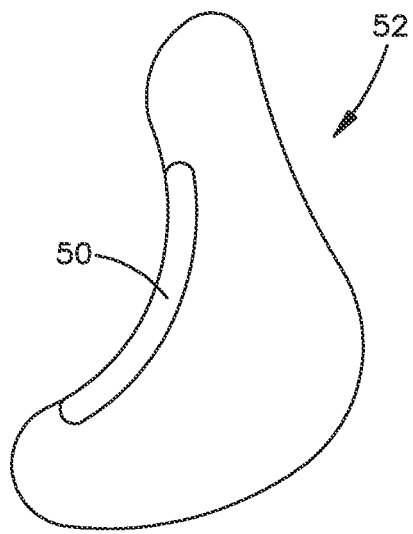
FIG. 8B is a medial view of the paranasal implant of FIG. 8A.
Figure 8C:
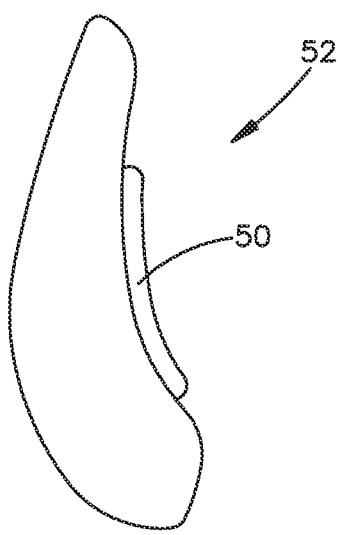
FIG. 8C is an anterior-lateral oblique view of the paranasal implant of FIG. 8A.

According to another aspect of the present invention, the implants may contain registration features that are provided to align with or abut specific features of the facial skeleton. In one embodiment, the invention relates to craniofacial implants having an inner contoured surface adapted to conform to boney structure and an outer contoured surface adapted to underlie soft tissue, and a flange 50 disposed along and extending from at least a portion of an edge thereof, the flange adapted to abut a landmark feature of the boney structure, to position initially the implant along at least one dimension. In certain embodiments, the implant can be an infraorbital rim implant 42 (see FIGS. 6A-6C), a mandible chin implant 23 (see FIGS. 7A-7C), or a paranasal implant 52 (see FIG. 8A-8C). For such embodiments, the flange 50 is positioned to abut the following respective landmark features: a lateral aspect of an orbital floor, an inferior border of a mandible body and a posterior border of a mandible ramus, and a pyriform aperture.

For example, according to a first embodiment of the invention, the placement of small flanges 50 on the posterior surface of certain facial implants (e.g., infraorbital rim, mandible and paranasal implants in the attached depictions)

allows accurate positioning relative to fixed anatomic landmarks. This allows accurate, symmetric three-dimensional placement of these implants.

For such implants, the flange 50 on the infraorbital rim implant abuts the lateral aspect of the orbital floor. The series of flanges on the mandible implant abut the inferior border of the mandible body and the posterior border of the mandible ramus to provide both vertical and transverse location registration. The flanges 50 on the lateral and medial aspects of the paranasal implants abut the pyriform aperture.

The flanges 50 or projections assure accurate, symmetric implant placement and avoid reliance on visual cues to position the implants, that can lead to inaccurate positioning. The flanges 50 result in more efficient, precise and predictable outcomes.

Figure 9:
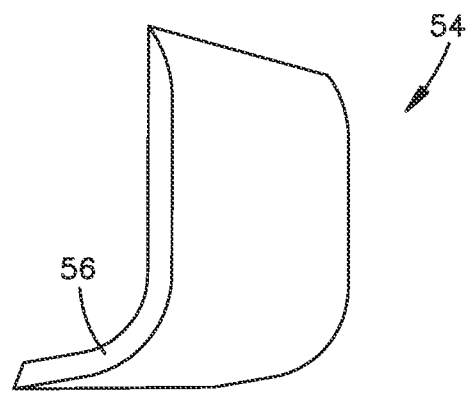
FIG. 9 is a lateral perspective view of a horizontal osteotomy implant in accordance with one embodiment of the invention.

Another embodiment of the invention relates to an implant that can be used with patients undergoing a horizontal osteotomy of the mandible that is being performed to change the location of the chin point with attached soft tissues. In this procedure, the chin point may be moved vertically sagittally, transversely, or in a combination of these directions. The osteotomy (i.e., the cut in the bone) creates a discontinuity along the inferior border of the mandible which is exaggerated by the movement of the chin segment. Depending on the amount of movement and the thickness of the overlying soft tissues, the resultant gap between the stationary mandible and its mobilized chin point may be visible and deforming. The horizontal osteotomy implant 54, depicted in FIG. 9, is adapted to bridge the gap between the two bone segments and restore a smooth mandibular border. In one embodiment, the implant 54 is configured to restore continuity in the mandible border after a sagittal osteotomy of the mandible.

The horizontal osteotomy implant 54 can be placed at the time that the horizontal osteotomy is performed or at a later time. Bone at either side of the osteotomy are exposed and freed of their attached soft tissues to allow placement of the implant. The horizontal osteotomy implant 54 has a flat surface that lies on the anterior face of each bone. It has a positioning ledge 56 (e.g., a 1 mm ledge) that wraps around the inferior border of each bone. The horizontal osteotomy implant 54 is adapted to bridge the gap between the two bone segments and restore a smooth mandible border. By bridging the osteotomy gap, the contour discontinuity caused by the separation of the two bones is smoothly transitioned and any otherwise discernible appearance thereof is eliminated. A precise and stable, regular border of the mandible is restored, since the implant is tailored to fit the precise anatomic needs of the situation and can be immobilized with screws, if necessary.

Use of the horizontal osteotomy implant 54 avoids the need to inject substances (e.g., hydroxyapatite, fat, and various filler materials) percutaneously into these defects, to attempt to soften the transition between the relocated chin point and mandible. Since the horizontal osteotomy implant 54 is placed under direct vision and can be immobilized with screws, an aesthetically appealing result can be ensured.

Cranial vault implants made through computer aided design and computer aided manufacturing (CAD/CAM) are traditionally made to fill exactly a skeletal defect in the cranial vault. Its position is stabilized with plates and screws. Prominent fixation hardware may erode through the overlying scalp closure leading to implant exposure and surgical failure. Another cause of surgical failure occurs in situations when there is space between the inner surface of the implant and the brain. Such a space (termed dead space) predispose to fluid accumulation and possible infection. Two versions of a cranial vault implant are described according to various embodiments of the invention to avoid these problems.

In general, FIG. 10 depicts one embodiment of a cranial implant 58 that includes a cranial body portion 60 adapted to fill substantially a cranial defect and a cranial thin edge portion 62 along at least a portion of a periphery thereof. The cranial thin edge portion 62 is adapted to receive therethrough fasteners to attach the cranial implant 58 to the cranium. In one embodiment, the cranial thin edge portion 62 is a taper.

Figure 10A:
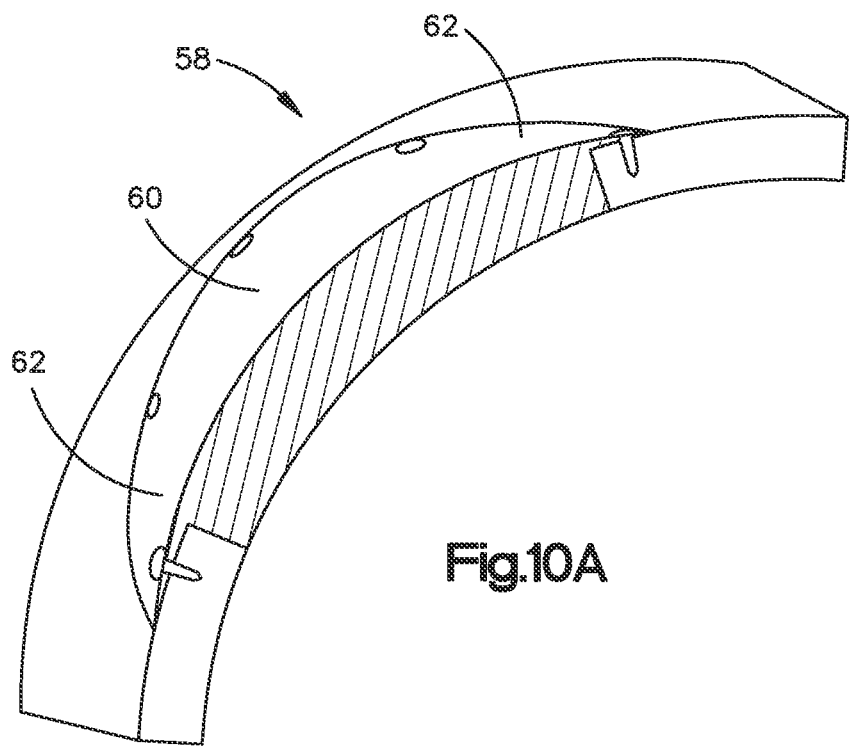
FIG. 10A is a depiction of a cranial implant in accordance with one embodiment of the invention.
Figure 11B:
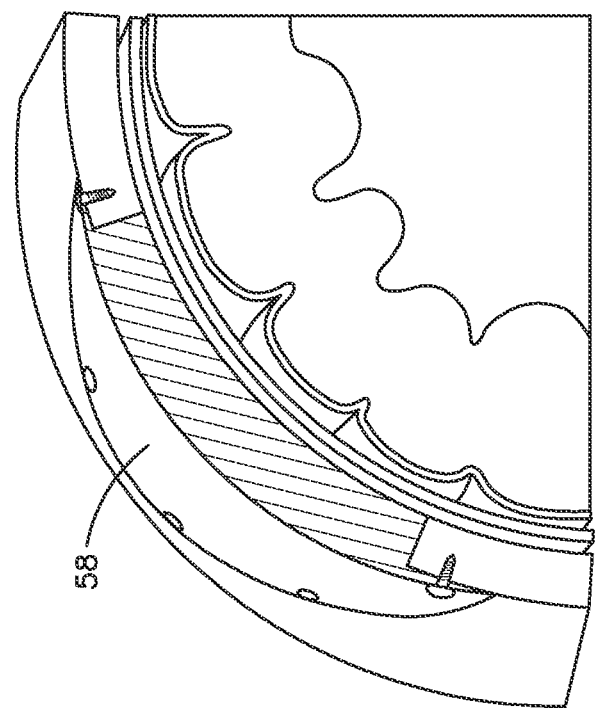
FIG. 11B is a cross-sectional view of the cranial implant of FIG. 11A denoting dead space.
Figure 11A:
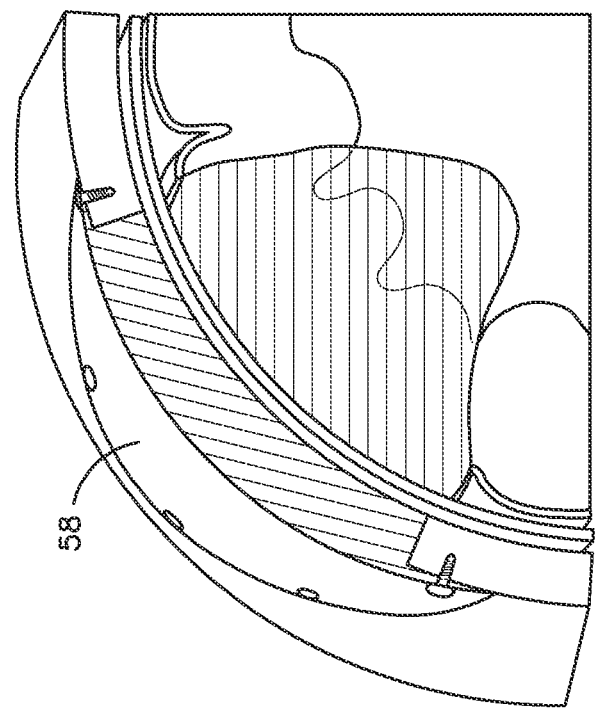
FIG. 11A is a cross-sectional view of a cranial implant in accordance with one embodiment of the invention.
Figure 11D:
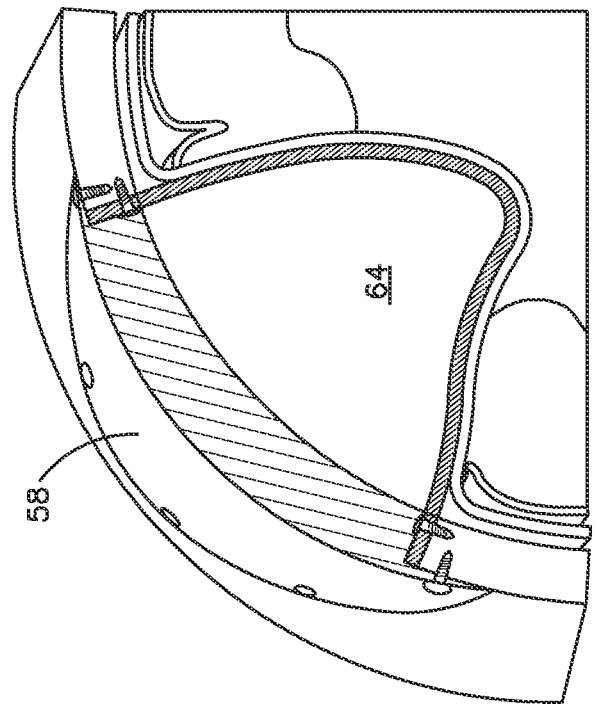
FIG. 11D is a cross-sectional view of the cranial implant of FIG. 11B with the cranial inner cup implant of FIG. 11C.
Figure 11C:
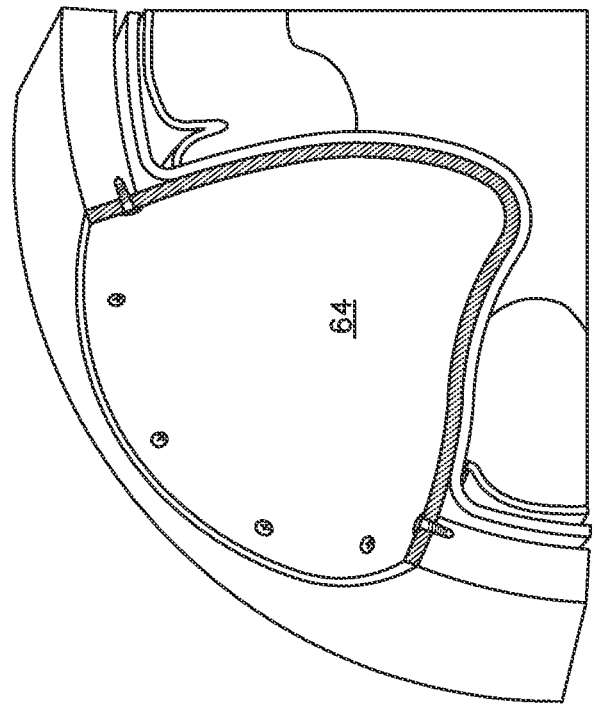
FIG. 11C is a cross-sectional view of a cranial inner cup implant filling the dead space of FIG. 11B.
Figure 12A:
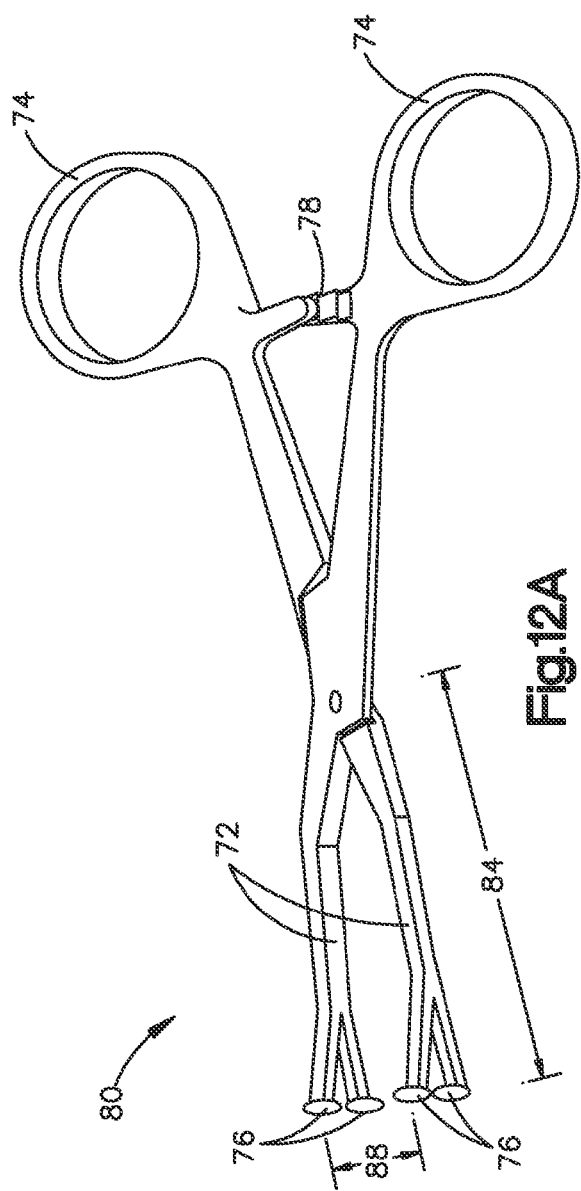
FIG. 12A is a top perspective view of an implant positioning forceps in accordance with one embodiment of the invention.
Figure 12B:
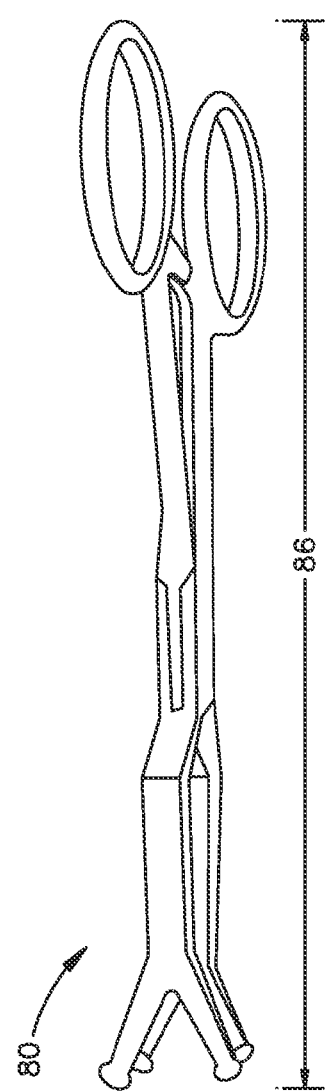
FIG. 12B is a side view of the implant positioning forceps of FIG. 12A.

In the embodiment depicted in FIG. 10A and FIG. 11A, the cranial implant 58 provides a location flange on a custom computer tomography generated cranial implant 58 that is designed to not only fill the cranial defect, but also to have the cranial thin edge portion 62 extending over the adjacent intact skull. The periphery of the cranial thin edge portion 62 can include openings, for instance through holes, that are configured to receive fasteners to attach the cranial implant 58 to the cranium. In one embodiment, the through holes can be predrilled prior to insertion of the implant. A computer topography scan can be used to determine a thickness of the cranium and based on the thickness of the cranium, fasteners can be chosen with a length such that the insertion of the fastener does not increase the implant profile. In one embodiment, the extension from the cranial thin edge portion 62 allows the implant to be fixed with lag screws, as opposed to higher profile plates and screws. Lag screws can be less prominent and less likely to erode through the overlying scalp. The extension from the cranial thin edge portion 62 also fills any gaps between the posterior surface of the scalp and any mismatch between the implant and the intact skull, that would otherwise be subject to soft tissue instability. The cranial implant 58 configuration allows the fixation hardware to be placed remote from the overlying scalp incision. It also decreases the likelihood of implant exposure, by extending the implant beyond the cranial defect and the overlying scalp incision, resulting in a more efficient, precise and predictable outcome than existing methods.

In one embodiment, the cranial thin edge portion 62 can have a thickness, tapering from up to about 1.5 mm or more to less than about 1 mm and have a lateral or radial extent of up to about 1 to 5 mm or more depending on the location of the scalp incision to the underlying area of skull reconstruction.

Referring to FIG. 10B, in another embodiment the cranial implant 58 can include a body portion 60 that defines an outer surface 57; an opposed inner surface 59; and a side wall 61 that extends between the outer surface 57 and inner surface 59. The side wall 61 defines a shape or an outer periphery of the body portion 60, for instance circular. In one embodiment the body portion 60 is configured such that the cranial implant 58 fits within, for instance entirely within, the cranial defect 63. As shown in the illustrated embodiment, the outer surface 57 does not extend beyond the outer surface of the cranium, and the side wall 61 does not extend beyond a periphery of the cranial defect 63. For example, the embodiment shown in FIG. 10B does not contain a cranial thin edge portion 62 as shown in FIG. 10A. The body portion 60 can further define openings 65, for instance predrilled holes, which are configured to receive a fastener, for instance a bone screw, such that when the cranial implant 58 has been secured to the cranium the fasteners are flush or countersunk with respect to the outer surface 57 of the cranial implant 58. The openings 65 can be oriented obliquely such that the opening 65 extends into the body portion 60 at an angle, for instance a non-normal angle, with respect to the outer surface 57. The opening 65 can extend through the body portion 60 and exit the body portion 60 at the side wall 61 such that a fastener inserted into the opening 65 can be secured to the cranium as shown.

Another cranial implant 58 embodiment addresses situations where there is an anticipated space ("dead space") between the inner surface of the implant and the brain (see FIGS. 11A-11D). In this instance a second implant piece is employed. An intracranial inner cup 64 can be designed using magnetic resonance (MR) or computed tomography (CT) data to adapt its convex surface to the outer concave surface of the brain, thus filling the dead space. Optional perforations in the floor of the implant allow sutures to secure the dura to the outer surface of the implant thus further eliminating potential for "dead space." The intracranial inner cup 64 can be shaped to allow it to be fastened with screws to the intact edge of the skull vault. The cranial implant 58 is fashioned to restore the skull vault contour and can be adapted to fit within the perimeter edge of the intracranial inner cup 64. In certain clinical situations, both the intracranial inner cup 64 and the cranial implant 58 could be fashioned into a single implant.

Another aspect of the invention relates to surgical instruments that aid in a more efficient and precise implant surgery. The surgeon often has very limited access to the skeletal area to be augmented. Due to the aesthetics involved in craniofacial surgery, placement of facial implants often entails less exposure by incision than would otherwise be desirable for surgical access. Once access is achieved, the implant is inserted and then must be positioned and adjusted until an optimal location is achieved. Thereafter, the implant needs to be held in proper position while it is being secured to the underlying bone, typically with screws. All such access for insertion, positioning, holding, and attachment is limited, to minimize the disturbance and scarring of the patient.

According to various embodiments of the invention, implant positioning forceps 80 and implant positioning clamps 82 (see FIGS. 13A-13B) are provided to facilitate more efficient, precise, and predictable surgery than heretofore has been achievable. In general, this aspect of one embodiment of the invention relates to a surgical instrument for manipulating a craniofacial implant, the instrument 80 including a pair of pivoting jaws 72 connected to a respective pair of finger grips 74, wherein each jaw includes a pair of spaced lobes 76 to provide up to four point contact and preclude substantially relative movement of a craniofacial implant disposed therebetween. A locking mechanism 78 is disposed between the finger grips to retain the finger grips in at least one predetermined relative spacing corresponding to a nominal jaw opening 88. In various embodiments, the surgical instrument 70 has a the nominal jaw opening value in a range of up to about 1 mm to about 10 mm or more, when the locking mechanism is engaged. Such embodiments may be particularly useful as implant positioning forceps 80, wherein the jaws are adapted to grasp solely a craniofacial implant therebetween. In various alternative embodiments, the surgical instrument has a nominal jaw opening value in a range of up to about 10 mm to about 50 mm or more, when the locking mechanism 35 is engaged. Such embodiments may be particularly useful as an implant positioning clamp 82, wherein the jaws are adapted to clamp a craniofacial implant to bone.

The implant positioning forceps 80 are configured and dimensioned to securely grasp facial implants during their placement or immobilization with screws. These implant positioning forceps 80 are especially useful in the midface and upper face, where the implant cannot be clamped to the bone (which is the preferred method in the mandible). The implant positioning forceps 80 have pivoting jaws 72 that grasp the anterior surface of the implant at various regions, to hold the implant in the forceps. The pivoting jaws 72 can be non-specific, in that they need not be designed to mate with a particular implant and therefore need not have extended jaw surfaces that are designed to conform to the surfaces of a particular implant. The finger grips 74 and locking mechanism 78 permit secure, stable holding of the implant and prevent implant movement during the stabilization process.

Available conventional forceps do not open their jaws sufficiently to grasp securely most facial implants, nor do they maintain stable purchase of the implant. The pivoting jaws 72 of the forceps 80 of one embodiment of the invention have a jaw opening distance 88 of about 4 mm, a pivot arm length 84 of about 70 mm, and an overall instrument length 86 of about 140 mm. The lobes 76 provide reliable retention, without structurally damaging the implant. Other dimensions are contemplated.

In those procedures where the undersurface of the bone is accessible (e.g., the mandible), an implant positioning clamp 82 according to one embodiment of the invention may be used, an example of which is shown in FIGS. 13A-13B. The implant positioning clamp 82 holds the implant in a stable desired position relative to the bone (e.g., the mandible) so that screws can be placed to permanently immobilize the implant. In one embodiment, in which the implant is applied to the anterior surface of the mandible, one of the pivoting jaws 72 purchases the anterior face of the implant and the other jaw purchases the posterior surface of the mandible. Accordingly, the pivoting jaws 72 of the clamp grasp the anterior surface of the implant and the undersurface of the bone to which it is being secured. The pivoting jaws 72 can be non-specific, in that they need not be designed to mate with a particular implant and therefore need not have extended jaw surfaces that are designed to conform to the surfaces of a particular implant. Its finger grip 74 and locking mechanism 78 prevent implant movement during the stabilization process. The implant positioning clamp 82 configuration and dimensions allow it to immobilize temporarily an implant to the surface of the mandible so that drill holes can be made through the implant and underlying bone in anticipation of fixing the implant to the mandible with screws. The pivoting jaws 72 of the implant positioning clamp 82 of one embodiment of the invention have a jaw opening distance 88 of about 20 mm, a pivot arm length 84 of about 60 mm, and an overall instrument length 86 of about 140 mm, as depicted. This technique affords stable, essentially hands-free immobilization of the implant during its securing to the facial skeleton.

Use of these implant positioning forceps 80 and implant positioning clamps 82 permit the implant to be readily positioned and held or immobilized during the final screw stabilization process. The surgical instruments prevent misalignment of the drill holes in the implant and underlying skeleton, which must be coaxial to allow screw purchase and proper implant immobilization. Movement of the implant during the fixation process with prior art techniques results in prolonged operating times and can result in implant malposition. Use of the surgical instruments avoids implant malposition, resulting in more efficient, precise, and predictable surgery.

FIGS. 12A-12B and FIGS. 13A-13B depict a pair of twin lobed jaws; however, a single lobed jaw could be paired with a twin lobed jaw, to provide three point contact with and retention of the implant, in either the forceps or clamp configurations. At least three point contact is desired, to constrain the implant from rotation when grasped with the forceps or when held in place with the clamp. Pivoting jaws 72 with more than two lobes 76 are also contemplated. In one embodiment of such clamp 82', an example of which is depicted in FIGS. 14A-14B, one pivoting jaw 72' contains at least three lobes 76' and the other pivoting jaw contains at least two lobes 76'. The lobes 76' interdigitate when closed. This clamp 82' can be useful in clamping a chin implant to a patient's chin. The jaw opening distance 88' should be suitably sized to provide effective clamping with the ratchet or other locking mechanism 78' engaged.

Further, as depicted, the orientation of the pivoting jaw 72 opening is perpendicular to the plane of the clamp 82 and is generally aligned with the longitudinal axis of the clamp 82. Instruments with other pivoting jaw opening orientations, angularly offset jaws, curved sections between the pivot and the jaws and/or finger grips, etc. are all contemplated and considered to be within the scope of the invention. Still other embodiments can include alternatives to finger grips (e.g., pistol grips) or eliminate the grips altogether, having a tweezer configuration with a spring loaded pivot or paired cantilevered arms joined at a point remote from the jaws. The ratchet or other locking mechanism 78 could then be disposed on the jaw side of the pivot or joined section. Various embodiments of the surgical instruments can be made of surgical stainless steel or other suitable material, for reuse. Alternatively, the surgical instruments can be made of suitable polymers or composite materials that may be sterilized and included in single-use surgical kits, and disposed of once the surgical procedure has been completed.

Figure 15:
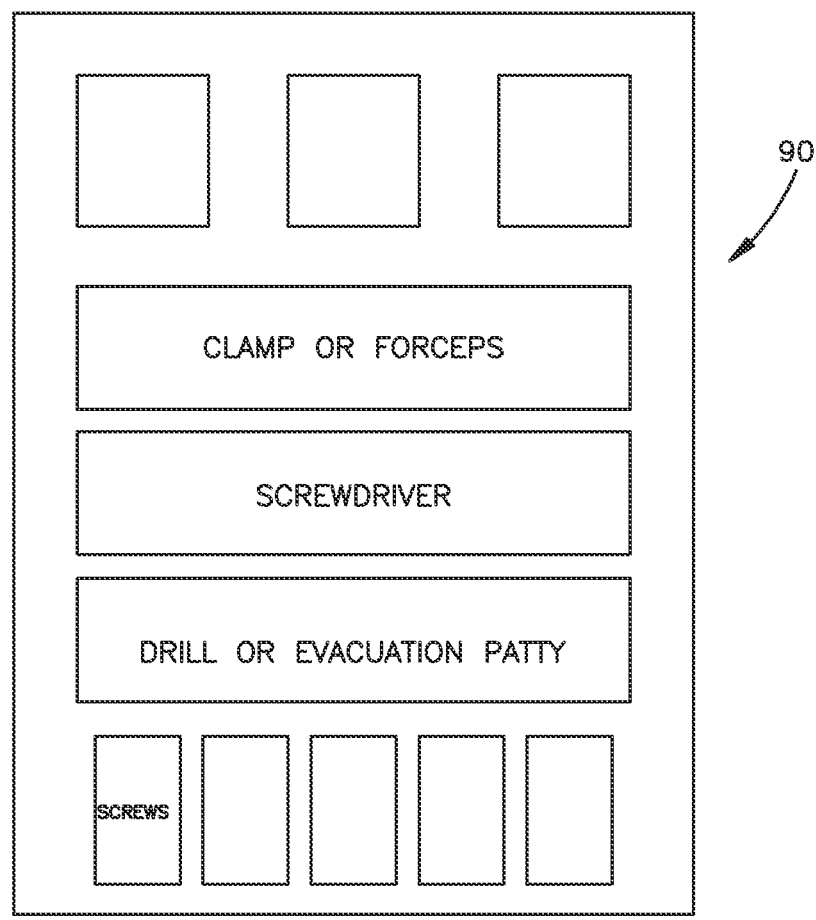
FIG. 15 is a depiction of a facial implant instrumentation system in accordance with one embodiment of the invention.
Figure 17C:
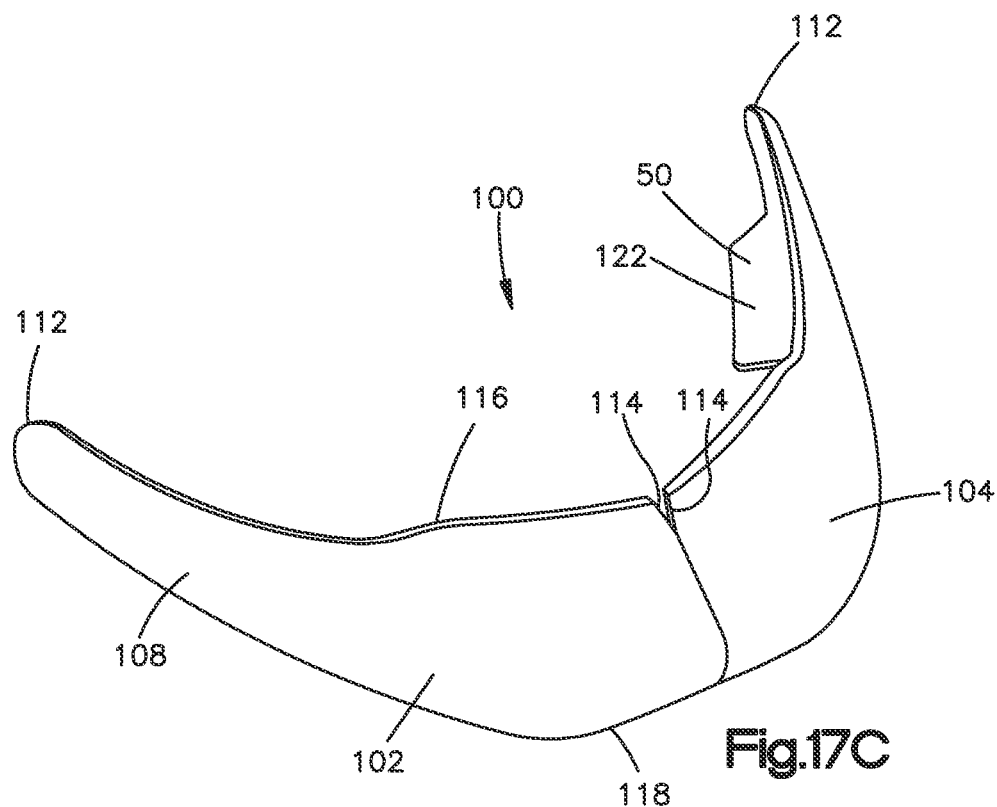
FIG. 17C is a perspective view of the mandible implant according to FIG. 17A in the assembled configuration.
Figure 17D:
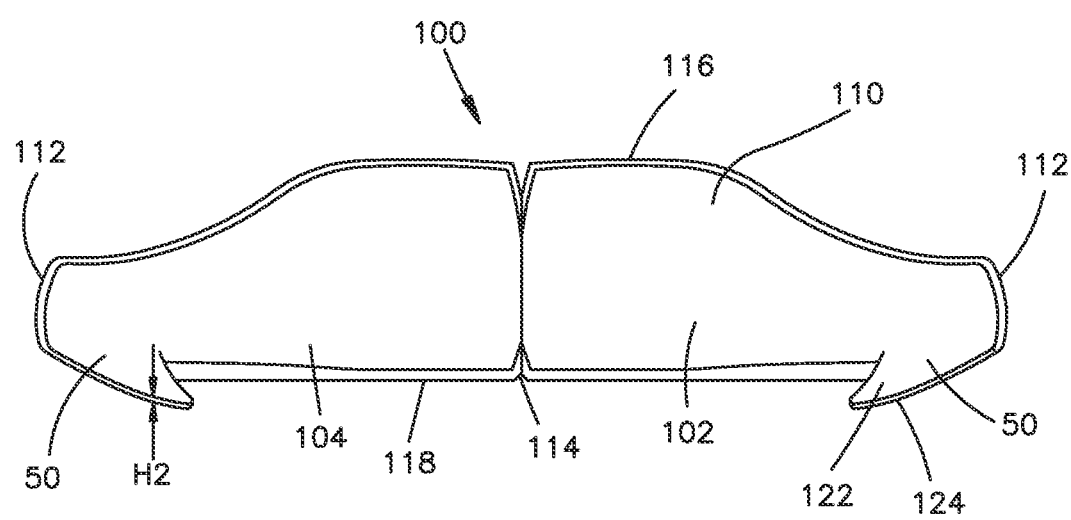
FIG. 17D is a rear view of the mandible implant illustrated in FIG. 17A.

Various aspects and embodiments of the present invention include a facial implant instrumentation system 90 to facilitate accurate placement and stabilization of facial implants. An example of this embodiment is depicted in the schematic of FIG. 15. Precise and stable positioning of implants is fundamental to the success of craniofacial implant surgery. In various embodiments the facial implant instrumentation system 90 can include in various combinations some or all of the following components, including periosteal elevators, straight and curved, to develop subperiosteal pockets for implants. The facial implant instrumentation system 90 can include an implant cutting board to contour implant with a scalpel or a burr prior to implantation. The cutting board may include a grid system that allows for symmetric contouring and accurate photographic documentation of the implants used. The facial implant instrumentation system 90 can include at least one implant positioning clamp 82 and/or implant positioning forceps 80 to immobilize implants during screw fixation. The facial implant instrumentation system 90 can include a 1.5 mm hand drill and a sterile battery powered micro drill system, which has a sleeve system for placement of non-sterile batteries into an otherwise sterile drill system. The facial implant instrumentation system 90 can include a 2.0 mm or other sized selection of screws (e.g. 6 to 14 mm length), screw drivers, a suction drain with trocar, and evacuation patty 92, one embodiment of which is depicted in FIG. 16. The evacuation patty 92 can be a cottonoid 94 that is embedded a perforated catheter 96 whose other end is attached to a conventional suction source mechanism. The evacuation patty 92, an example of which is depicted in FIG. 16, is adapted to gently remove fluids and smoke from the operative field.

As described hereinabove, surgery on the facial skeleton is usually made through remote incisions. As a result the surgical field for example, the deep orbit, is visible only to the surgeon. The evacuation of blood or smoke from use of electrocautery becomes difficult. The evacuation patty 92 removes these elements from the operative field without input from an assistant or the operator. The evacuation patty 92 in one embodiment consists of a neurosurgical cottonoid 94 of dimensions of approximately about 1×1.5 cm. Imbedded in its central aspect is a perforated end of a 19 gauge plastic catheter 96. The other end of the catheter 96, which is approximately 35 cm long, is coupled to standard operating room suction tubing 98 which, in turn is connected to a suction mechanism. Placement of the small cottonoid 94 after wetting in the operative does not obscure visualization of the field. Suction applied to the wetted cottonoid 94 allows evacuation of fluids in the field through capillary action. For an example of a device used to maintain a clear field during microsurgical vessel anastomosis, see Zienowicz R J, Jupiter J B, Yaremchuk M J: A microsurgical suction mat. *J Hand Surg.*, 19A, 5 19-520 (1 994), the disclosure of which is incorporated herein in its entirety.

Referring to FIGS. 17A-17G, a mandible implant 100 (also known as a chin implant) can include a first body portion 102, a second body portion 104 and a joining element 106 that is configured to attach and secure the first and second body portions 102 and 104 together. The first and second body portions 102 and 104, respectively, can be symmetrical, for instance, minor images of each other, such that the first and second body portion 102 and 104, respectively, each contain similar shapes and features. Therefore any description of the structure or elements of the first body portion 102 below can also be applicable to the second body portion 104, unless otherwise indicated. It should be appreciated that the first body portion 102 and the second body portion 104 may have slight differences, such as the exact size and shape of the body portions 102 and 104 and the inclusion or positioning of various structure carried by one or both of the first and second body portions 102 and 104, as described in more detail below.

The first body portion 102 defines a pair of opposed ends, such as a first or proximal end that can be configured as an anterior base 114, and a second or distal end that can be configured as a posterior tip 112 that is opposite and spaced from the anterior base 114 along a central axis 113 that can be shaped as desired so as to correspond to an underlying boney structure. For instance, in accordance with the illustrated embodiment, the central axis 113 is curved. The first body portion 102 further defines a first surface such as an inner surface 110, which is a bone-facing surface in accordance with the illustrated embodiment, and a second surface such as an outer surface 108 that is opposite and spaced from the inner surface 110 along a lateral or first direction 115 that is substantially perpendicular to the central axis 113. The inner and outer surfaces 110 and 108 can extend between the posterior tip 112 and the anterior base 114, and in accordance with the illustrated embodiment extend, for instance continuously, from the posterior tip 112 to the anterior base 114. The first body portion 102 can further define a first edge such as a superior edge 116 and a second edge such as an inferior edge 118 that is opposite and spaced from the superior edge 116 along a transverse second direction 117 that is substantially perpendicular to both the axis 113 and the first direction. The superior and inferior edges 116 and 118 can extend between the posterior tip 112 and the anterior base 114, and in accordance with the illustrated embodiment extend, for instance continuously, from the posterior tip 112 to the anterior base 114. The superior and inferior edges 116 and 118 can further extend between the inner and outer surfaces 110 and 108, and in accordance with the illustrated embodiment extend, for instance continuously, from the inner surface 110 to the outer surface 108. Accordingly, the outer surface 108 and inner surface 110 can each extend substantially vertically from the superior edge 116 to the inferior edge 118 and substantially along the central axis 113 the posterior tip 112 to the anterior base 114.

The first body portion 102 can be tapered such that superior edge 116 and the inferior edge 118 taper toward each other along a direction from the anterior base 114 toward the posterior tip 112. Furthermore, one or both of the superior edge 116 or the inferior edge 118 can be feathered. For instance, one or both of the inner or outer surfaces 110 and 108 can taper toward each other along the second direction 117 from the central axis 113 toward the superior edge 116, and one or both of the inner or outer surfaces 110 and 108 can taper toward each other along the second direction 117 from the central axis 113 toward the inferior edge 118. In accordance with one embodiment, one or both superior or inferior edges 116 or 118 can abut the underlying bone once the mandible implant 100 has been implanted to an underlying human mandible.

The first body portion 102 is shaped to correspond to that of the underlying human mandible. For example, the inner surface 110 can define a contour having a concavity 119 such that when the inner surface 110 is positioned adjacent to the underlying human mandible the inner surface 110 mates flush with the mandible. The inner surface 110 being configured to mate flush with the mandible can result in better congruence, for instance less gapping and more predictability of augmentation, between the inner surface 110 and the mandible. The outer surface 108 can also define a curvature 121 that is convex. In one embodiment, when the underlying mandible is damaged or deformed, the outer surface 108 can be configured with a curvature 121 such that the outer surface 108 does not extend substantially parallel to a corresponding outer surface of the underlying mandible. The curvature 121 can be configured to restore a normal mandible appearance, for instance such that the mandible is symmetrical. In another embodiment, when the outer surface of the mandible is largely intact with only minor deformation, the outer surface 108 can be configured with a curvature 121 such that the outer surface extends substantially parallel to a corresponding outer surface of the underlying mandible in order to minimize the change in shape or appearance of the patient's mandible after the mandible implant 100 has been implanted to the mandible. Additionally, the inferior edge 118 can be inclined along a direction from the anterior base 114 toward the posterior tip 112 so as to extend substantially parallel to a complementary inclination of an inferior border of a patient's mandible. The first portion 102 can further include a lip 129 positioned adjacent the inferior edge 118 with a shape complementary to that of the inferior border of the patient's mandible.

The first body portion 102 defines a height H1 that can be defined between the superior edge 116 and the inferior edge 118 along the second direction 117. It should be appreciated that the height H1 at the base 114 can be as desired so as to accommodate a wide range of sizes and shapes of an underlying mandible. It may be desirable to provide the mandible implant 100 having a first height H1 for a patient with a large, square chin, and to provide the mandible implant 100 having a second height H1 that is smaller than the first height H1 for a patient having a smaller chin A mandible implant 100 that has a shape that is configured to correspond to that of an underlying mandible can lead to a more stable and aesthetically pleasing result after implantation. It should thus be appreciated that a kit can include a plurality of mandible implants 100 of various shapes and sizes (for example with different heights H1) sized to fit various sized mandibles.

The first body portion 102 can also include a registration feature that is configured to align with or abut complementary landmark features of the facial skeleton. As shown, the registration feature can be configured as a flange 50 that extends out from the inner surface 110 substantially along the first direction 115. For instance, the flange 50 can extend from the inner surface 108 along a direction from the outer surface toward the inner surface. The flange 50 can define a first or superior surface such as an abutment surface 122, and an opposed second or inferior surface such as an exterior surface 124 that is spaced from the abutment surface 122 along the second direction 117. The flange 50 can define a height H2 that is defined between the abutment surface 122 and the exterior surface 124 along the second direction 117. The abutment surface 122 can be contoured to correspond to a complementary landmark feature of the facial skeleton.

The flange 50 can be angularly offset with respect to the inner surface 110 and substantially rigidly positioned such that the abutment surface 122 of the flange 50 is configured to abut the complementary landmark feature of the underlying mandible so as to prevent movement of the implant 100 relative to the underlying mandible in at least one direction when the implant 100 is positioned against the underlying mandible. For example, the abutment surface 122 can be configured to abut the inferior border of an underlying mandible so as to interfere with the underlying mandible when a force is applied to the implant 100 along a superior direction, along the direction 117. Accordingly, movement of the implant 100 in the superior direction, along the second direction 117, is prevented when the implant 100 is positioned adjacent the underlying mandible. It can further be said that the flange 50 can be angularly offset to the inner surface 110 and positioned such that the abutment surface 122 is configured to abut a landmark feature of an underlying mandible such that movement of the implant 100 in a direction parallel to the inner surface 110 is prevented when the inner surface 110 is positioned adjacent the underlying mandible.

As shown, the flange 50 can extend out from the inner surface 110 at a location adjacent the inferior edge 118. Alternatively, the flange 50 can extend out from the inner surface 110 at any position along the height H1 of the implant 100 from the inferior edge 118 to the superior edge 116 (including the inferior edge 118 and the superior edge 116). In one embodiment, the flange 50 can extend substantially perpendicular from the inner surface 110 such that the flange 50 is positioned adjacent the inferior edge 118 of the first body portion 102 such that flange 50 will abut the inferior border of the underlying mandible. Alternatively, the implant 100 can define any angle as desired between the flange 50 and the inner surface 110. Furthermore, the flange 50 can be positioned at any location on the inner surface 110 between the superior edge 116 and the inferior edge 118 such that the flange 50 aligns with or abuts the complementary landmark feature of the underlying facial skeleton. It should be appreciated in accordance with the illustrated that the flange 50 can be devoid of bone fixation holes that receive a bone fixation member, such as a nail or a screw, to attach the flange to the underlying mandible. It should be appreciated, however, in certain embodiments that the flange 50 can include bone fixation holes as desired.

The first body portion 102 can include a recess 120 that extends into the anterior base 114 substantially along the central axis 113. The recess 120 can be sized to receive the joining element 106. For instance, the recess 120 can be sized substantially equal to the joining element 106 such that the joining element 106 is press-fit into the recess 120 so as to attach the first and second body portions 102 and 104. For instance, the joining element 106 can be positioned within the recess 120 at various depths along the central axis 113 such that the first body portion 102 and the second body portion 104 can be spaced apart along an adjustable distance. For instance, a variable sized gap can extend between the anterior bases 114 of the first and second body portions 102 and 104 when the first and second body portions 102 and 104 are attached to each other. For example, the joining element 106 can be inserted into the recess 120 of the first and second body portions 102 and 104 to a first depth such that the anterior bases 114 of the first and second body portions 102 and 104 abut each other, such that the variable sized gap is zero. Alternatively, the joining element 106 can be inserted into the recess 120 of the first and second body portions 102 and 104 to a second depth less than the first depth such that the anterior base of the first and second body portions 102 and 104 are separated by the gap along a distance greater than zero. This adjustability can provide for a number of different jaw widths to be accommodated by the mandible implant 100.

In accordance with the illustrated embodiment, the joining element 106 can be separate from one or both of the first and second body portions 102 and 104. In accordance with one embodiment, joining element 106 can be integral and monolithic with one of the first and second body portions 102 and 104 (see FIG. 17G), such that the other of the first and second body portions 102 and 104 carries the complementary recess 120 that is configured to receive the joining element 106. The complementary recess 120 can be integral with the other of the first and second body portions 102 and 104 as illustrated, or can be defined by a second member that is attached to the other of the first and second body portions 102 and 104.

Referring to FIGS. 18A-18D, a malar implant 140 can include a body 142 and one or more registration features such as flange 50. The body 142 defines an outer edge such as a peripheral edge 148. The body 142 further defines a first surface such as an inner surface 146, which is a bone facing surface in accordance with the illustrated embodiment, and a second surface such as an outer surface 144 that is opposite and spaced from the inner surface 146 along a first direction 147. The inner and outer surfaces 146 and 144 can extend, for instance continuously, from the peripheral edge 148 at a first location to the peripheral edge at a second location spaced apart from the first location. The body 140 defines a shape that can be configured to correspond to that of a human malar bone (also referred to as the zygomatic bone or cheek). For example, the inner surface 146 can define a contour having a concavity 155 such that when the inner surface 146 is positioned adjacent to an underlying human malar the inner surface 146 mates flush with the malar bone. The outer surface 144 can also define a curvature 157 that is convex so as to extend substantially parallel to a corresponding outer surface of the underlying malar bone in order to minimize the change in shape of the appearance of the patient's cheek after implantation of the malar implant 140 has been implanted to the malar. Additionally, the peripheral edge 148 can be configured to closely conform to adjacent underlying bone structures, such as the zygomatic arch or the lateral infraorbital rim, to minimize the change in shape of the appearance of the patient's cheek after implantation of the malar implant 140. It should appreciated that the shape of the body 142 defined by the peripheral edge 148 can be as desired so as to accommodate a wide range of sizes and shapes of an underlying malar.

The body 142 defines a width W1 that can be defined between the inner and outer surfaces 146 and 144 along the first direction 147. It may be desirable to provide the malar implant 140 having a first width W1 at a location roughly near a middle of the body 142 and a second width W1 at a location adjacent the peripheral edge 148 such that the body 142 is tapered and the width W1 decreases closer to the peripheral edge 148 of the malar implant 140. In one embodiment, the peripheral edge 148 can be feathered such that the width W1 tapers down to the peripheral edge 148 such that there is no visible border between the malar implant 140 and the underlying bone once the malar implant 140 has been implanted. Alternatively, the width W1 can be constant across the entire malar implant 140.

The body 142 can also include at least one registration feature that is configured to align with or abut complementary landmark features of the facial skeleton. The registration feature can be configured as a flange 50 that extends out from the inner surface 146 or, as shown in the illustrated embodiment from the peripheral edge 148. For instance the flange can extend from the inner surface 146 or the peripheral edge 148 substantially along a second direction, such as a direction of elongation 149, which is perpendicular to the first direction 147. The flange 50 can extend out from the inner surface 146 or the peripheral edge 148 a distance D1 along the direction of elongation 149. As shown in the illustrated embodiment, the body can further include a second flange 50 that is spaced from the at least one flange. The second flange extends away from the peripheral edge along a third direction that is angularly offset with respect to the first direction, wherein the plane further intersects the second flange. In one embodiment the plane is oriented substantially perpendicular to the third direction. In another embodiment, the third direction is substantially normal to the plane. The third direction can be parallel to the second direction, or the third direction can be angularly offset with respect to the second direction, for instance such that the second and third directions converge.

The flange 50 can include an abutment surface 152 and an opposed exterior surface 154. The flange 50 defines a width W2 that can be defined between the abutment surface 152 and the exterior surface 154 along the first direction 147. The width W2 of the flange 50 can be the same as the width W1 of the malar implant 140 at the position where the flange 50 extends out from the body 142. Alternatively, the width W2 of the flange 50 can be different than the width W1 of the malar implant 140, such that the width W2 of the flange 50 is either greater than or less than the width W1 of the malar implant 140 where the flange 50 extends out from the body 142. The abutment surface 152 can be contoured to correspond to a landmark feature of the facial skeleton. The description of the flange 50 as described in regards to FIGS. 18A-18D is applicable to the registration features and flanges 50 referred to in the other embodiments within the present disclosure.

The flange 50 can be angularly offset with respect to the inner surface 146 and substantially rigidly positioned such that the abutment surface 152 of the flange 50 is configured to abut the complementary landmark feature of the underlying malar bone so as to prevent movement of the implant 140 relative to the underlying malar in at least one direction when the implant 140 is positioned adjacent the underlying malar. For example, the abutment surface 152 can be configured to abut a landmark feature of the underlying malar such that movement of the implant 140 in one direction along a superior-inferior axis is prevented when the implant 140 is positioned adjacent the underlying malar bone. It can further be said that the flange 50 can be angularly offset to the inner surface 146 and positioned such that the flange 50 is configured to abut a landmark feature of the underlying malar bone such that movement of the implant 140 in a direction parallel to the inner surface 146 is prevented when the inner surface 146 is positioned adjacent the underlying malar bone.

In one embodiment, the flange 50 can be angularly offset to the inner surface 146 and positioned such that the abutment surface 152 of the flange 50 abuts an underlying malar bone such that movement of the malar implant 140 in a direction parallel to the inner surface 146 is prevented when the inner surface 146 is positioned adjacent the underlying malar bone. The flange 50 can extend substantially perpendicular to the inner surface 148 or alternatively, the flange 50 can extend at any other angle from the inner surface 148. As shown the flange 50 can extend out from the peripheral edge 148. Alternatively, the flange 50 can extend out from the body 142 at a position either spaced apart from or adjacent to the peripheral edge 148 of the malar implant 140. The flange 50 can be positioned such that the abutment surface 152 will abut a landmark feature of the underlying cheek bone when the malar implant is positioned adjacent the malar bone. The landmark feature of the underlying malar bone can include, but is not limited to: a zygomatic arch; a lateral infraorbital rim; and other craniofacial bones. The malar implant 140 can include more than one flange 50 positioned such that each of the flanges 50 will abut either the same or a different landmark feature of the underlying bone. For example, in one embodiment the malar implant 140 can include first and second flanges 50 positioned such that when the malar implant is implanted adjacent an underlying malar bone, the abutment surface 152 of the first flange 50 abuts an underlying zygomatic arch and the abutment surface 152 of the second flange 50 abuts an underlying lateral infraorbital rim such that movement of the of the malar implant 140 in a direction parallel to the inner surface 146 is prevented.

In accordance with one embodiment, the craniofacial implant 140 is configured to be implanted between a boney structure and soft tissue. The implant 140 includes an inner contoured surface 146 that is adapted to conform to the underlying malar bone when the malar implant 140 is implanted between the boney structure and the soft tissue. The implant can further include an outer contoured surface 144 that is adapted to underlie the soft tissue when the implant is implanted between the boney structure and the soft tissue, and a peripheral edge 148 disposed between the inner contoured surface 146 and the outer contoured surface 144. The implant 140 can further include at least one flange 50 disposed along and extending from at least a portion of the peripheral edge 148. Each of the at least one flange 50 can be positioned and adapted so as to abut a landmark feature of the underlying malar when the malar implant 140 is implanted between the boney structure and the soft tissue such that abutment between the flange 50 and the landmark feature prevents movement of the malar implant 140 in a direction parallel to the inner contoured surface. The malar implant 140 can further define a line 160 that extends from the peripheral edge 148 at a first location 162 to the peripheral edge 148 at a second location 164, the line intersecting with the at least one flange 50 and the at least one flange 50 extends along the direction of elongation 149 and the line 160 is substantially perpendicular to the direction of elongation 149.

Furthermore, as described above, the inner surface 146 can be curved with a concavity 155. In accordance with the illustrated embodiment, the concavity 155 can be partially bound by the flange 50. Additionally, the inner surface 146 can be concave with respect to a plane P1 that can be oriented such that one side of the plane P1 faces the concavity 155, extends through at least a select one or more of the flanges 50, and is substantially perpendicular to the direction of elongation 149 of the select one or more of the flanges 50. Additionally still, the body 142 can define a plane P2 that contacts the peripheral edge 148 at three or more locations on the peripheral edge 148, such as a first location 170, a second location 172 and a third location 174, the plane P2 intersects a select one or more of the flanges 50, and is angularly offset, for instance substantially perpendicular, with respect to the direction of elongation 149 of the select one or more of the flanges 50.

In one embodiment, proper positioning of the malar implant 140 can be verified, for example the flange 50 is abutting the zygomatic arch (or other landmark feature of the underlying malar), through an incision just lateral to the lateral canthus (referred to as a "crow's feet incision"). Once the malar implant 140 has been inserted and positioned as desired, a portion of the malar implant 140 may overlie with an inferior aspect of an orbital rim of the underlying bone structure. This overlying portion of the malar implant 140 can be extended superiorly toward the level of the canthus. A fixation device, for instance a screw, could then be passed through the extended portion to secure the malar implant 140 in a desired position. In one embodiment, the extended portion can be thin with no flange 50.

While there have been depicted and described various embodiments, dimensions, and materials of the various embodiments and aspects of the invention, unless otherwise stated these are exemplary in nature and the scope of the invention is not limited thereto.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein, unless otherwise indicated. Accordingly, those skilled in the art will realize that the invention is intended to encompass all modifications and alternative arrangements included within the spirit and scope of the invention, for instance as set forth by the appended claims.

What is claimed:

1. A craniofacial implant comprising:
   a first body portion including a superior edge and an inferior edge, which taper towards each other from an anterior base at a proximal end of the first body portion to a posterior tip at a distal end of the first body portion, and defining, between the superior and inferior edges, a bone facing inner surface shaped to correspond to a first portion of a mandible and a first opposed outer surface, each of the first portion of the mandible and the first opposed outer surface located on a first side of a human cranium;
   a second body portion including a superior edge and an inferior edge, which taper towards each other from an anterior base at a proximal end of the second body portion to a posterior tip at a distal end of the second body portion, and defining, between the superior and inferior edges, a bone facing inner surface shaped to correspond to a second portion of the mandible and a second opposed outer surface, each of the second portion of the mandible and the second opposed outer surface located on a second side of a human cranium mirroring the first side, the anterior base of at least one of the first and the second body portion including a recess extending therein;

a joining element configured to secure the first and second body portions to each other, the joining element received in the recess in the anterior base of at least one of the first and second body portions; and at least one registration flange on each body portion, each flange having a superior surface and an inferior surface, the superior surface of each flange positionable at a location on the inner surface, between the superior and the inferior edges, of a corresponding body portion, such that the superior surface is abuttable against a landmark bone feature of the mandible so as to prevent movement of the implant relative to the mandible in at least one direction when the implant is positioned adjacent the mandible, wherein each flange extends substantially perpendicularly from the inner surface of the corresponding body portion.

2. The craniofacial implant as recited in claim 1, wherein the flange extends from the bone facing inner surface along a direction from the outer surface toward the inner surface.

3. The craniofacial implant as recited in claim 1, wherein the joining element is integral with one of the first and second body portions.

4. The craniofacial implant as recited in claim 1, wherein the first and second body portions are substantially symmetrical.

5. The craniofacial implant as recited in claim 1, wherein the abutment surface is contoured to correspond to a complementary contour of the landmark bone feature.

6. The craniofacial implant as recited in claim 1, wherein the at least one direction is parallel to the inner surface of the body portion that the flange extends from.

7. The craniofacial implant as recited in claim 1, wherein the first body portion defines an anterior end and a posterior end, such that both the inner and outer surfaces and the inferior and superior edges extend between the anterior and posterior ends substantially along a central axis, and at least one of the anterior and posterior edges is tapered toward the other of the anterior and posterior edges along a direction from the anterior end toward the posterior end.

8. The craniofacial implant as recited in claim 1, wherein the central axis extends between the anterior and posterior ends, and the central axis is curved.

* * * * *